(12) United States Patent
Florescu

(10) Patent No.: US 10,433,847 B2
(45) Date of Patent: Oct. 8, 2019

(54) PLATFORM DEVICE AND METHOD OF USE TO ASSIST IN ANASTOMOSIS FORMATION

(71) Applicant: Board of Regents of the University of Nebraska, Lincoln, NE (US)

(72) Inventor: Marius C. Florescu, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 581 days.

(21) Appl. No.: 15/104,372

(22) PCT Filed: Dec. 17, 2014

(86) PCT No.: PCT/US2014/070928
§ 371 (c)(1),
(2) Date: Jun. 14, 2016

(87) PCT Pub. No.: WO2015/095378
PCT Pub. Date: Jun. 25, 2015

(65) Prior Publication Data
US 2016/0324521 A1    Nov. 10, 2016

Related U.S. Application Data

(60) Provisional application No. 61/917,081, filed on Dec. 17, 2013.

(51) Int. Cl.
*A61B 17/11*    (2006.01)
*A61B 17/34*    (2006.01)
(Continued)

(52) U.S. Cl.
CPC .......... *A61B 17/11* (2013.01); *A61B 17/3468* (2013.01); *A61B 2017/00004* (2013.01);
(Continued)

(58) Field of Classification Search
CPC .......... A61B 17/11; A61B 2017/00004; A61B 2017/1107; A61B 17/122; A61B 17/10; A61B 17/128; A61B 17/1285; A61F 2/88
(Continued)

(56) References Cited

U.S. PATENT DOCUMENTS 3,882,862 A    5/1975    Berend
4,553,545 A    11/1985    Maass et al.
(Continued)

OTHER PUBLICATIONS

Akoh, "Prosthetic arteriovenous grafts for hemodialysis", J. Vasc. Acess Acess, 10(3), pp. 137-147, Jul.-Sep. 2009.
(Continued)

*Primary Examiner* — Diane D Yabut
*Assistant Examiner* — Majid Jamialahmadi
(74) *Attorney, Agent, or Firm* — Suiter Swantz pc llo

(57) ABSTRACT

There is described a platform device for use in forming an anastomosis and maintaining a desired curvature of a lumen in a desired shape during an anastomosis assistance period. The platform is formed from one or more bioabsorbable or biodegradable polymer filaments. There is also described a method for inserting a platform device for use in creation of an arteriovenous fistula by identifying a candidate artery and a candidate vein and dissecting the candidate vein. Next, inserting a platform device into the vein and creating a breach in the candidate artery at a desired angle and location. Next, introducing the platform device and vein into the candidate artery and forming the platform device into a curvature angle selected to minimize turbulent blood flow in an anastomosis formed by the vein and the artery. The platform may also be used to maintain potency of supply blood vessels and/or organ blood vessels or the lumens during an organ transplant procedure.

14 Claims, 25 Drawing Sheets

(51) Int. Cl.
*A61B 17/00* (2006.01)
*A61F 2/966* (2013.01)
*A61F 2/88* (2006.01)

(52) U.S. Cl.
CPC .......... A61B 2017/1107 (2013.01); A61B 2017/1135 (2013.01); A61F 2/88 (2013.01); A61F 2/966 (2013.01)

(58) Field of Classification Search
USPC .......... 606/142, 139, 143, 129, 200, 153; 607/127
See application file for complete search history.

(56) References Cited

U.S. PATENT DOCUMENTS

| | | | |
|---|---|---|---|
| 4,813,925 A | 3/1989 | Anderson, Jr. et al. | |
| 5,246,445 A * | 9/1993 | Yachia | A61F 2/88 604/104 |
| 5,372,600 A | 12/1994 | Beyar et al. | |
| 5,476,505 A | 12/1995 | Limon | |
| 5,676,685 A | 10/1997 | Razavi | |
| 5,824,053 A | 10/1998 | Khosravi et al. | |
| 5,935,145 A | 8/1999 | Villar et al. | |
| 6,063,111 A * | 5/2000 | Hieshima | A61B 17/12022 606/191 |
| 6,375,606 B1 | 4/2002 | Garibaldi et al. | |
| 6,709,452 B1 | 3/2004 | Valimaa et al. | |
| 6,746,464 B1 | 6/2004 | Makower | |
| 6,872,218 B2 | 3/2005 | Ferrera et al. | |
| 6,926,724 B1 | 8/2005 | Chu | |
| 6,974,473 B2 | 12/2005 | Barclay et al. | |
| 7,691,140 B2 | 4/2010 | Bates et al. | |
| 7,828,814 B2 | 11/2010 | Brenneman et al. | |
| 7,867,272 B2 | 1/2011 | Niermann | |
| 8,062,328 B2 | 11/2011 | Hallisey | |
| 8,535,345 B2 | 9/2013 | Desai et al. | |
| 2003/0225425 A1 * | 12/2003 | Kupiecki | A61B 17/11 606/153 |
| 2005/0177246 A1 | 8/2005 | Datta et al. | |
| 2005/0228472 A1 | 10/2005 | Case et al. | |
| 2005/0273121 A1 * | 12/2005 | Sato | A61B 17/11 606/153 |
| 2006/0193892 A1 | 8/2006 | Furst et al. | |
| 2006/0241675 A1 | 10/2006 | Johnson et al. | |
| 2007/0100437 A1 | 5/2007 | Welborn et al. | |
| 2007/0255253 A1 | 11/2007 | Jones et al. | |
| 2008/0200979 A1 | 8/2008 | Dieck et al. | |
| 2008/0306580 A1 | 12/2008 | Jenson et al. | |
| 2009/0054966 A1 | 2/2009 | Rudakov et al. | |
| 2009/0131972 A1 | 5/2009 | Wallace et al. | |
| 2010/0010613 A1 | 1/2010 | Dorn | |
| 2010/0030319 A1 | 2/2010 | Weber | |
| 2010/0100170 A1 | 4/2010 | Tan et al. | |
| 2010/0268316 A1 * | 10/2010 | Brenneman | A61B 17/083 623/1.11 |
| 2011/0046720 A1 | 2/2011 | Shalev et al. | |
| 2011/0166642 A1 | 7/2011 | Ehr et al. | |
| 2011/0184347 A1 | 7/2011 | Mason | |
| 2012/0029614 A1 | 2/2012 | Burnside et al. | |
| 2014/0163586 A1 * | 6/2014 | Holt | A61B 17/064 606/151 |
| 2014/0257369 A1 | 9/2014 | Leopold et al. | |

OTHER PUBLICATIONS

Anneaux et al., "Bioabsorbable polymers as biomaterials", Poster Presentation, 43 pages.
Eberhart et al., "Bioresorbable polymeric stents, current status and future promise", J. Biomater. Sci. Polymer Edn., 14(4), pp. 299-312, 2003.
Eggers, "Has the incidence of end-stage renal disease in the USA and other countries stabilized?", Curr. Opin. Nephrol. Hypertens., 20(3), pp. 241-245, May 2011.
Grassmann et al., "ESRD patients in 2004; global overview of patient numbers, treatment modalities and associated trends", Nephrology Dial. Transplant., 20(12), pp. 2587-2593, Dec. 2005.
Hakaim et al., "Improved patency of prosthetic arteriovenous grafts with an acute anastomotic angle and flow diffuser", J. Vasc. Surg., 37(5), pp. 1032-1035, May 2003.
Haruguchi et al., "Intimal hyperplasia and hemodynamic factors in arterial bypass and arteriovenous grafts; a review", J. Artif Organs, 6(4), pp. 227-235, 2003.
Liou et al., "intra-aneurysmal flow with helix and mesh stent placement across side-wall aneurysm pore of a straight parent vessel", J. Biomech. Eng., 126(1), pp. 36-43, Feb. 2004 (Abstract Only).
Malek et al., "Hemodynamic shear stress and its role in atherosclerosis", JAMA, 282(21), pp. 2035-2042, Dec. 1, 1999.
Paryab et al., "Uniform expansion of a polymeric helical stent", J. Med. Devices, 6(2), May 14, 2012, (Abstract Only).
Zamir, "The role of shear forces in arterial branching", J. Gen. Physiol. Physiology, 67(2), pp. 213-222, 1976.
International Search Report dated Apr. 23, 2015 for PCT/US2014/070928.

* cited by examiner

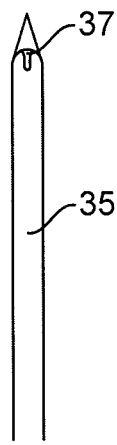
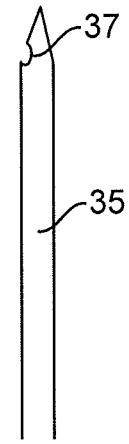
FIG. 12A  FIG. 12B
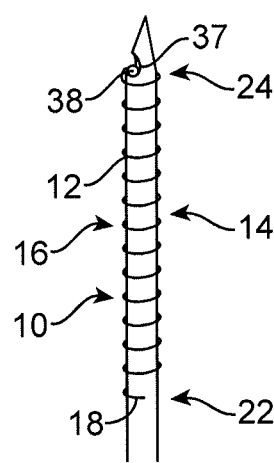
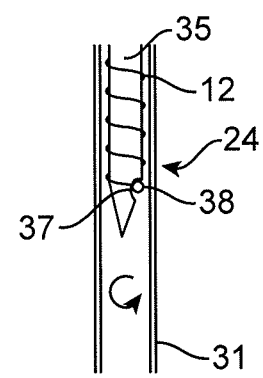
FIG. 12C  FIG. 12D

PLATFORM DEVICE AND METHOD OF USE TO ASSIST IN ANASTOMOSIS FORMATION

CROSS REFERENCE TO RELATED APPLICATIONS

This application claims the benefit under 35 U.S.C. 119 of U.S. Provisional Patent Application No. 61/917,081, filed Dec. 17, 2013, titled "DEVICE TO ASSIST IN ARTERIO-VENOUS FISTULA FORMATION" and U.S. Provisional Patent Application No. 62/032,818, filed Aug. 4, 2014, titled "IMPROVED DEVICE TO ASSIST IN FISTULA FORMATION," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

STATEMENT AS TO FEDERALLY SPONSORED RESEARCH

None.

FIELD

The present invention relates to medical devices used to assist medical personnel in vascular access procedures, particularly those procedures involving the creation of an anastomosis platform device embodiments of the present invention include a structure to support a vessel during and after surgical intervention. Specifically, one embodiment of the platform device structure supports the joining of blood vessels, like in the formation of an anastomosis, or an arteriovenous fistula.

BACKGROUND

Nearly 2.5 million patients worldwide suffer from End Stage Renal Disease (ESRD). To treat ESRD, patients are either subjected to a kidney transplant or undergo hemodialysis. Though acting as artificial kidneys, dialysis machines are not implanted in the body; instead, they require durable external access points to the body's circulatory system, often in the form of an arteriovenous fistula (AVF). An AVF is created via an artificial junction, or "anastomosis", between an artery and a vein which is used to increase the volume of blood flow through the vein. Over time, the increase in blood flow volume increases the size of the vein.

As the circulatory system is typically understood, blood flows away from the heart through a series of arteries. Arteries branch off to even smaller vessels called capillaries, where nutrients such as oxygen are delivered to muscle tissues and cells. Thereafter, deoxygenated blood continues to flow through capillaries, and eventually returns to larger vessels called veins. Veins carry deoxygenated blood back to the heart and lungs, where the blood is reoxygenated and continues through the circulatory system.

In order to create an arteriovenous fistula, this process is short-circuited. There are a number of locations within the body where an arteriovenous fistula may be created, but for hemodialysis patients the most common location is on the non-dominant forearm. In order to create the fistula, the patient is generally put under anesthesia and a small incision is made to open up the patient's forearm in order to expose a superficial vein. The cephalic vein is tied off from blood flow and subsequently severed. The proximal (that is, the segment of the cephalic vein which maintains blood flow to the heart) is then sutured directly to the nearby radial artery and blood flow through the vein is resumed.

Because the normal capillary diffusion system is eliminated, blood flow through the cephalic vein is increased beyond what the vessel is accustomed to. In order to accommodate the increased blood flow, the size of the cephalic vein begins to expand over a period of weeks until the vein itself begins to bulge from under the skin of the patient, a process called AVF maturation. When the bulging vein has reached sufficient size, medical personnel implant dialysis needles into the vein such that dialysis machines can be connected to the patient's circulatory system.

The best hemodialysis vascular access is an Arteriovenous Fistula (AVF). In order to create an AVF, it is required to connect an artery with a vein. After the surgery 6-8 weeks are needed for fistula maturation. During the maturation the venous segment of the fistula is growing. The growing of the vein is triggered by the increased blood flow through the vein. The laminar flow of the blood through the fistula is responsible to initiate a cascade of events leading the fistula vein growth and fistula maturation. Conversely a turbulent blood flow will stimulate the vein to stenose preventing the fistula from maturing.

Unfortunately, there are a number of complications that may occur in the creation of an arteriovenous fistula. For example, the typical AVF requires 6-8 weeks to mature to a size and strength sufficient to support insertion of a dialysis needle. Further, 45-55% of AVFs fail to sufficiently mature, requiring the creation of a new arteriovenous anastomosis and a further 6-8 weeks of maturation time before a new fistula is created.

Many of the AVF created do not mature to a usable AVF. In US, the AVF maturation rate ranges between 45-55%. Most of the times the cause of nonmaturation is the presence of perianastomotic stenosis (narrowing of the vessel in the area of the surgical anastomosis) found to be present in 75% of nonmaturing AVF. The trauma of the surgery and the turbulent blood flow are believed to be responsible for the development of perianastomotic stenosis. The turbulent flow involved in the lack of fistula maturation might be created by the steep angle the vein is anastomosed to the artery. FIG. 1A illustrates a vein 31 formed into a curvature 23 attached to an artery 32. The attached vein 31 forms a steep anastomosis angle 36 approaching 90 degrees. FIG. 1B illustrates the degraded situation of the anastomosis of FIG. 1A after a few weeks. FIG. 1B illustrates a partially matured arteriovenous anastomosis D formed by an artery A and a vein C. There is a panastomosis B formed in the vein C. Note as well the steep angle 36 of the anastomosis D.

AVF developmental complications are generally attributed to increases in blood flow shear stress, i.e. turbulence, created due to the artificial nature of the arteriovenous anastomosis. As the blood flows through the artery and into the vein, it has been observed to eddy, or pool, instead of flowing smoothly through the anastomosis. This turbulent flow causes blood vessel stenosis—a narrowing of the vessel which limits the available flow rate. As stenosis occurs in the fistula anastomosis, the volume of blood flow is reduced, and the vessel may fail to stretch to the volume required to support a dialysis access port. It is therefore desirable to design a device which minimizes the amount of turbulent blood flow through the AVF anastomosis.

SUMMARY OF THE DISCLOSURE

In general, in one embodiment, a platform device includes a bioabsorbable filament selected to begin degrading within one week of implantation into a lumen of a human or animal body and to be substantially completely absorbed by the animal or human body after an anastomosis assistance period has elapsed; and a coil structure having a length along a major axis and a width along a minor axis formed by a plurality of windings of the filament about the major axis wherein the filament width and the spacing between windings relates to the coil structure length and the dimension of the windings across the minor axis relates to the coil structure width.

This and other embodiments can include one or more of the following features. In one aspect, the anastomosis assistance period can be less than three weeks. In another aspect, the anastomosis assistance period can be less than five weeks. In a further aspect, when the coil structure is in a stowed configuration the plurality of windings can provide an overall cylindrical shape to the coil structure. In an alternative aspect, when the coil structure is in a deployed configuration the spacing between adjacent windings can be different that the spacing between adjacent windings in the stowed configuration. In yet another aspect, when the coil structure is in a deployed configuration the coil structure can form a selected anastomosis angle having an inner radius of curvature and an outer radius of curvature wherein the spacing between adjacent windings along the inner radius of curvature can be less than the spacing between adjacent windings along the outer radius of curvature. In still another aspect, a distal aperture of the platform can be formed into an oblong or ovoid shape prior to forming an anastomosis. In one aspect, a distal aperture of the platform can be formed into a shape selected based on a dimension or a shape of another lumen at an anastomosis site. In another aspect, the bioabsorbable filament can be a biocompatible polymer selected from the group consisting of: a (poly)lactic acid, a poly(lactic-co-glycolic acid), a polyglycolide, a copolymer, and a cross-linked polymer. In a further aspect, the bioabsorbable filament can be a biocompatible polymer having an in vivo degradation rate corresponding to an anastomosis assistance period that can correspond to the time required for fistula formation. In an alternative aspect, when the platform device is in a deployed configuration a distal aperture of the platform device can have one or more windings of decreasing dimension across the minor axis. In yet another aspect, when the platform device is in a deployed configuration one or more windings of the proximal portion of the coil structure can form a non-circular opening. In still another aspect, the distal aperture can have a circumference and a shape selected based on an anastomosis angle of the platform device in use to form an arteriovenous fistula. In one aspect, when the platform device is in a deployed configuration shaped into a curvature angle for use to form a fistula, a portion of the curvilinear connectors along an inner radius of the curvature angle can be shorter than a portion of the curvilinear connectors along an outer radius of the curvature angle. In another aspect, when the platform device is in a deployed configuration within the lumen to facilitate formation of an arteriovenous fistula, one or more of the windings can be manipulated to provide a provide a lumen having a tilted conical trunk and an obtuse curvature angle. In a further aspect, when the platform device is formed to facilitate formation of an arteriovenous fistula a proximal aperture of the platform device can have an ovoid or oblong shape. In an alternative aspect, in use to facilitate formation of an arteriovenous fistula a plurality of distal windings can provide the coil structure with a generally circular distal portion and a plurality of proximal windings provide the coil structure with a generally non-circular proximal opening. In yet another aspect, in use to facilitate formation of an arteriovenous fistula the circumference of a distal portion of the coil structure within the lumen beyond a dissection location can be less than the circumference of a distal portion of the coil structure adjacent to an anastomosis connection location. In still another aspect, the platform device can further include an obdurator and can have a distal end, a proximal end, and an overall shape adapted to receive the plurality of windings. In one aspect, the obdurator can have a tip on the distal end and an increasing diameter of the overall shape towards the proximal end. In another aspect, the obdurator can include a mating feature shaped to receive a corresponding mating feature formed on a distal portion of the filament. In a further aspect, the obdurator distal in diameter can be smaller than the obdurator proximal end diameter. In an alternative aspect, the diameter increase along the obdurator can be gradual. In yet another aspect, the diameter increase can be a step. In still another aspect, the step can be sized to be smaller than a filament width. In still another aspect, the step can be sized to be greater than or about the same as a filament width. In one aspect, the platform device can further include an introducer sheath having a lumen dimensioned to receive the filament loaded onto the obdurator.

In general, in one embodiment, a method for inserting a platform device for use in creation of an arteriovenous fistula, including the steps of: identifying a candidate artery and a candidate vein; dissecting the candidate vein; inserting a platform device into the vein; creating a breach in the candidate artery at a desired angle and location; forming an anastomosis by attaching the vein to the artery; and manipulating the platform device into a shape selected to minimize turbulent blood flow in the anastomosis.

This and other embodiments can include one or more of the following features. In one aspect, after the manipulating step the anastomosis can be formed by the vein and the artery forms an anastomosis angle between 90 degrees and 180 degrees. In another aspect, the anastomosis angle can be between 100 degrees and 130 degrees. In a further aspect, the method of the forming step can further include suturing the vein to the artery without incorporating any of the platform device. In an alternative aspect, the method of the forming step can further include suturing the vein to the artery so that substantially all of the platform device is within the vein. In yet another aspect, the method can further include expending an angioplasty balloon to expand the vein before or after the inserting step. In still another aspect, the method can further include expending a plurality of coils within the platform during the expanding step. In one aspect, after the forming step the spacing can be increased between adjacent windings in a first portion of the platform device and the spacing can be decreased between adjacent windings in a second portion of the platform device. In another aspect, after the forming step or the manipulating step a circumference can be formed by a plurality of windings in a proximal portion of the platform device attached to the artery can be larger than a circumference formed by a plurality of windings in a distal portion of the platform device within the vein. In a further aspect, after the forming step or the manipulating step the distal aperture can be formed by a plurality of the distal most windings of the platform device attached to the artery form an imperfectly circular shape. In an alternative aspect, the vein can be a cephalic vein and the artery can be a radial artery. In yet another aspect, the method of the forming step can further include applying heat to the platform device before, after or during any of the steps. In still another aspect, the method can further include after the inserting step, tying together a portion of a first filament of the platform device to a portion of a second filament of the platform device. In one aspect, the method can further include after the inserting step, adjusting the size of the platform device by removing a portion of a first filament of the platform device or a second filament of the platform device. In another aspect, the method can further include forming a desired anastomosis angle by inserting a shape tool into the platform device proximal aperture. In a further aspect, the forming step can be performed after the inserting step. In an alternative aspect, the method can further include before the inserting step: loading the platform onto an obdurator and during the inserting step rotating the obdurator.

In general, in one embodiment, a platform device for coupling one lumen to another, including: a biodegradable polymer filament having properties selected so as to remain within the one lumen for at least one week and be substantially absorbed or biodegraded by three weeks; the filament having a cross-section dimension of from about 0.004 inches to about 0.007 inches; the filament formed into a coil structure of a plurality of windings about a central longitudinal axis a length along a central longitudinal axis from a proximal end to a distal end.

This and other embodiments can include one or more of the following features. In one aspect, the filament can have a circular cross-section shape, an oval cross-section shape, an elliptical cross-section shape, a rounded rectangular cross-section shape, a tear drop cross-section shape, or a ellipsoid cross-section shape. In another aspect, the filament can further include a first portion having a first overall width and a first cross-section shape and a second portion having a second overall width and the second cross-section shape. In a further aspect, the first overall filament width can be greater than the second overall filament width. In an alternative aspect, the width of the coil structure can be between 2 mm to 4.5 mm. In yet another aspect, the first cross-section shape can be the same as the second cross-section shape and the first overall width is greater than the second overall width. In still another aspect, the first overall width can be about the same as the second overall width and the first cross-section shape can be different than the second cross-section shape. In one aspect, when the platform device is in use within a lumen of the body the overall diameter of the coil structure can increase from the proximal end to the distal end of the platform device. In another aspect, the overall diameter can be from about 2 mm to about 6 mm. In a further aspect, when the platform device is in use within a lumen of the body the overall diameter of the coil structure can decrease from the proximal end to the distal end of the platform device. In an alternative aspect, the overall diameter can be from about 2 mm to about 6 mm. In yet another aspect, a proximal or distal terminal end of the filament can be modified to reduce a risk of penetration of an adjacent lumen wall while the platform device can be implanted within the lumen. In still another aspect, the proximal or distal terminal end can be bent into a curve, formed into a rounded portion, formed into a bulbous portion, or covered with a ball.

In general, in one embodiment, a platform device for coupling one lumen to another, including: a first and a second biodegradable polymer filament having properties selected so as to remain within the one lumen for at least one week and be substantially absorbed or biodegraded by three weeks; the first and the second filaments having a cross-section dimension of from about 0.002 inches to about 0.007 inches; the first and the second filaments formed into a pair of adjacent coil structures each one having a plurality of windings about a common central longitudinal axis a length along the common central longitudinal axis from a proximal end to a distal end.

This and other embodiments can include one or more of the following features. In one aspect, the first or the second filament can have a circular cross-section shape, an oval cross-section shape, an elliptical cross-section shape, a rounded rectangular cross-section shape, a tear drop cross-section shape, or a ellipsoid cross-section shape. In another aspect, the first or the second filament can further include a first portion having a first overall width and a first cross-section shape and a second portion having a second overall width and the second cross-section shape.

In a further aspect, the first or the second filament having a first overall filament width can be greater than the second overall filament width. In an alternative aspect, the first filament can have a cross section dimension greater than the second filament cross section dimension. In yet another aspect, when the platform device can be in use within a lumen of the body the overall diameter of the coil structures can increase from the proximal end to the distal end of the platform device. In still another aspect, the overall diameter can be from about 2 mm to 6 mm at a distal portion to about 2 mm to 6 mm at a proximal portion. In one aspect, when the platform device can be in use within a lumen of the body the overall diameter of the coil structures can decrease from the proximal end to the distal end of the platform device. In another aspect, the overall diameter can be from about 2 mm-4 mm at a distal portion to about 4 mm-6 mm at a proximal portion. In a further aspect, a proximal or distal terminal end of the first or the second filament can be modified to reduce a risk of penetration of an adjacent lumen wall while the platform device is implanted within the lumen. In an alternative aspect, the proximal or distal terminal end of a first filament or a second filament can be bent into a curve, formed into a rounded portion, formed into a bulbous portion, or covered with a ball. In yet another aspect, a portion of the first filament can be tied to a portion of the second filament at a proximal end or a distal end of the platform device. In still another aspect, a portion of the first filament can be tied to a portion of the second filament at the proximal platform end and at the distal platform end.

In general, in one embodiment, a method of forming an anastomosis with a bioabsorbable platform device, comprising: dissecting a portion of a lumen within a body to form a proximal fixed lumen portion and a distal unattached lumen portion having an open proximal end; inserting the platform device into the open proximal end and along the unattached lumen portion; and positioning a portion of the platform device to maintain the open proximal end in a configuration selected for coupling the open proximal end to an anastomosis location.

This and other embodiments can include one or more of the following features. In one aspect, the method after the inserting step can further include advancing the platform device within the lumen until a portion of the platform device is within the proximal fixed lumen portion. In another aspect, the method can further include after the positioning step and with the platform device present within the unattached lumen portion, coupling the open lumen end to the anastomosis location. In a further aspect, after the positioning step, the step of bending an end of the filament in the platform device can be performed. In an alternative aspect, after the positioning step, there can be a step of tying together the first filament of the platform device and a second filament of the platform device. In yet another aspect, the method can further include cutting a portion of the unattached lumen portion to shape the open proximal end for coupling to the anastomosis location. In still another aspect, after the coupling step the position of a portion of the platform device within the unattached lumen can be adjusted to form a desired angle between the unattached lumen portion and the anastomosis location. In one aspect, the desired angle can be an angle selected to produce a desired flow pattern within the lumen. In another aspect, the anastomosis can be formed with a vein and an artery, a blood vessel and a vessel of a transplant organ. In a further aspect, the method can further include inserting a platform device into a vein or artery of a transplant organ.

In an alternative aspect, the length from the platform proximal portion to the distal portion can be from about 2 cm, 3 cm, 4 cm, 5 cm, 6 cm, 7 cm, 8 cm, 9 cm, 10 cm, 11 cm or 12 cm before implantation into a lumen. In yet another aspect, the length from the platform proximal portion to the distal portion can be from about 2 cm, 3 cm, 4 cm, 5 cm, 6 cm, 7 cm, 8 cm, 9 cm, 10 cm, 11 cm or 12 cm after implantation into a lumen.

In any of the above or in still further embodiments, there may be included one or more or an advantageous combination of the following features. In one aspect, there is a tubular body, or a filament formed into windings of a coiled body or braid or a platform device can be constructed of a biocompatible polymer selected from the group consisting of a (poly)lactic acid (PLA), a polylactic-co-glycolic acid) (PLGA), a polyglycolide (PGA), a copolymer, a poly-1-lactic acid (PLLA) and a cross-linked polymer. In another aspect, the tubular body can be constructed from a biocompatible polymer having an in vivo degradation rate corresponding to the time required for fistula formation. In still another aspect, a filament used in the devices described herein may be constructed of a biocompatible/bioabsorbable polymer comprising a (poly)lactic acid, a poly(lactic-co-glycolic acid), a polyglycolide, a copolymer, or a cross-linked polymer and optionally including copolymerization with lower levels of L-lactide, such as for example 90/10 glycolide/L-lactide, 80/20 glycolide/L-lactide so that the filament is metabolized within 3 weeks, or within 2 weeks, or, within 2-3 weeks, or, substantially completely metabolized at or before a fistula maturation of a fistula formed using the filament or platform device. In still other embodiments, a bioabsorbable polymer filament comprises 100% PLGA. In still other embodiments, a bioabsorbable polymer filament comprises 90/10 PGA/PLLA. In still other embodiments, a bioabsorbable polymer filament comprises 90/10 PGA/PLGA. In still other embodiments, a bioabsorbable polymer filament comprises a lactide/glycolide mole ratio of 50/50. In still other embodiments, a bioabsorbable polymer filament comprises 50/50 PLLA-PGA. In still other exemplary embodiments, a tubular body, or a filament formed into windings of a coiled body or braid or a platform device can be constructed of a biocompatible, biodegradable polymer comprising a (poly)lactic acid (PLA), or a poly(lactic-co-glycolic acid) (PLGA), or a polyglycolide (PGA), or a copolymer, or a poly-1-lactic acid (PLLA) or a cross-linked polymer selected to provide initial support at an anastomosis site with a bioabsorption or degradation rate selected to have the filament or structure formed by the filament substantially completely or sufficiently absorbed or metabolized such that the filament or structure produced by the filament does not impede the flow of fluids within a lumen that contained the implanted filament based structure. In still other alternatives, the filament or platform device comprises a hydrolytic, bio-absorbable polymer or co-polymer blend that is substantially completely absorbed within three weeks of being implanted into a human or animal body. In still another alternative, the filament or platform device comprises a hydrolytic, bio-absorbable polymer or co-polymer blend that is substantially completely absorbed within two to three weeks of being implanted into a human or animal body. In still other variations of any of the above or in other alternatives, a filament as used herein may undergo a form of mechanical disruption to accelerate polymer hydrolysis.

In one aspect, there is also a platform as described above that includes an anti-inflammatory composition on or within all or a portion of a filament.

In another aspect, there is a platform as described above that includes an anti-proliferative composition on or within all or a portion of a filament.

In yet another aspect, there is a platform as described above that includes an anti-thrombotic composition on or within all or a portion of a filament.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 9A is a cross-section view of a three rounded cross-section filaments of a platform device in contact with a section of a lumen wall.

FIG. 9B is a cross-section view of a three rounded cross-section, multiple layer or composite filaments of the platform device in contact with a section of a lumen wall.

FIG. 9C is a cross-section view of a three rectangular or ribbon shaped cross-section filaments of the platform device in contact with a section of a lumen wall.

FIG. 9D is a cross-section view of three braided filaments of a platform device in contact with a section of a lumen wall.

FIGS. 12A and 12B are top and side views respectively of an obdurator having a receiver for a filament to secure a platform onto the obdurator.

FIG. 12C is a side view of the obdurator of FIGS. 12A, 12B with a platform device loaded onto and secured to the obdurator.

FIG. 12D is a partial section view of the loaded obdurator of FIG. 12C being rotated into a lumen for the deployment of the platform.

FIGS. 18A1-18G are various views of a platform and insertion device during the steps of the method of FIG. 17.

DETAILED DESCRIPTION

Figure 1A:
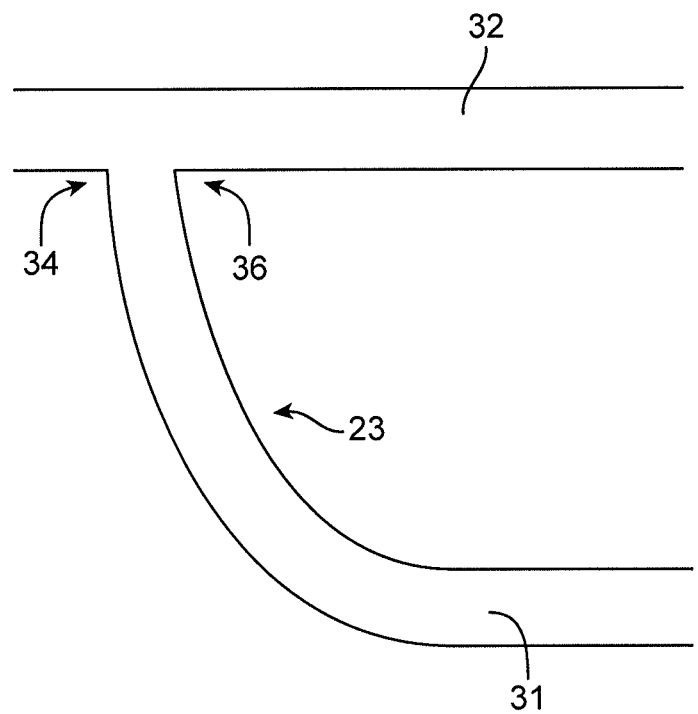
FIG. 1A is a simplified top view of an arteriovenous anastomosis just after surgery.

In one embodiment of the present invention, a platform device 10 used to support the formation of an anastomosis is provided. The platform device 10 may be composed of a filament of a polymeric material selected from a number of biodegradable compounds which are identified based on their in vivo degradation rate, biocompatibility, malleability, or other relevant characteristics. The body of the device 10 may further be formed from a series of coils 14 of a biodegradable compound. The device 10 may further be formed with concentric coils, producing a narrow distal end and a wider proximal end (see e.g., FIGS. 2D and 5).

In another embodiment of the present invention, the device is shaped to form a conical trunk, wherein the aperture of the device at the anastomosis has a greater circumference than the remaining portion of the device.

In yet another embodiment of the present invention, the device may be bent or curved such that it adopts an angle of anastomosis which promotes laminar, non-turbulent, blood flow through the arteriovenous interface. The curve may not be formed into the device at production, but the device may be made of materials selected so that the operator can form it to a curve of her choosing during surgical procedure. For example, the device 10 can be formed of a material that is malleable at a low temperature but a temperature warmer than body temperature.

In general, in one embodiment of a platform device 10 the present invention configured for use with an arteriovenous fistula, device 10 includes a generally tubular body formed from loops or windings 16 that form the tubular or coil structure 14 body. In one embodiment, the loops are formed from a single filament of biodegradable material as described above. At both the proximal and distal ends of the filament, appropriate modifications are present in order to prevent the filament from penetrating the wall of the blood vessel. For example, the tip of the filament is formed to be a ball with a circumference larger than the gauge of the filament (see FIGS. 3A-3E).

This and other embodiments can include one or more of the following features. For example, a tubular body, or a filament formed into windings of a coiled body or braid or a platform device can be constructed of a biocompatible polymer selected from the group consisting of a (poly)lactic acid (PLA), a poly(lactic-co-glycolic acid) (PLGA), a polyglycolide (PGA), a copolymer, a poly-1-lactic acid (PLLA) and a cross-linked polymer. In another aspect, the tubular body can be constructed from a biocompatible polymer having an in vivo degradation rate corresponding to the time required for fistula formation. In still another aspect, a filament used in the devices described herein may be constructed of a biocompatible/bioabsorbable polymer comprising a (poly)lactic acid, a poly(lactic-co-glycolic acid), a polyglycolide, a copolymer, or a cross-linked polymer and optionally including copolymerization with lower levels of L-lactide, such as for example 90/10 glycolide/L-lactide, 80/20 glycolide/L-lactide so that the filament is metabolized within 3 weeks, or within 2 weeks, or, within 2-3 weeks, or, substantially completely metabolized at or before a fistula maturation of a fistula formed using the filament or platform device. In still other embodiments, a bioabsorbable polymer filament comprises 100% PLGA. In still other embodiments, a bioabsorbable polymer filament comprises 90/10 PGA/PLLA. In still other embodiments, a bioabsorbable polymer filament comprises 90/10 PGA/PLGA. In still other embodiments, a bioabsorbable polymer filament comprises a lactide/glycolide mole ratio of 50/50. In still other embodiments, a bioabsorbable polymer filament comprises 50/50 PLLA-PGA. In still other exemplary embodiments, a tubular body, or a filament formed into windings of a coiled body or braid or a platform device can be constructed of a biocompatible, biodegradable polymer comprising a (poly)lactic acid (PLA), or a poly(lactic-co-glycolic acid) (PLGA), or a polyglycolide (PGA), or a copolymer, or a poly-1-lactic acid (PLLA) or a cross-linked polymer selected to provide initial support at an anastomosis site with a bioabsorption or degradation rate selected to have the filament or structure formed by the filament substantially completely or sufficiently absorbed or metabolized such that the filament or structure produced by the filament does not impede the flow of fluids within a lumen that contained the implanted filament based structure. In still other alternatives, the filament or platform device comprises a hydrolytic, bio-absorbable polymer or co-polymer blend that is substantially completely absorbed within three weeks of being implanted into a human or animal body. In still another alternative, the filament or platform device comprises a hydrolytic, bio-absorbable polymer or co-polymer blend that is substantially completely absorbed within two to three weeks of being implanted into a human or animal body. In still other variations of any of the above or in other alternatives, a filament as used herein may undergo a form of mechanical disruption to accelerate polymer hydrolysis.

In another aspect, the distal aperture can have a circumference and a shape selected based on an anastomosis angle of the device in use to form an arteriovenous fistula. In still another aspect, when the device is in a deployed configuration shaped into a curvature angle for use to form a fistula, a portion of the curvilinear connectors along an inner radius of the curvature angle can be shorter than a portion of the curvilinear connectors along an outer radius of the curvature angle. In a further aspect, when the device is formed to facilitate formation of an arteriovenous fistula the device has a tilted conical trunk and an obtuse curvature angle. In yet another aspect, when the device is formed to facilitate formation of an arteriovenous fistula a distal aperture of the device can have an ovoid or oblong shape. In a further aspect, in use to facilitate formation of an arteriovenous fistula, there can be a circular opening on the proximal end of the tubular body and a non-circular opening on the distal end of the tubular body. In yet a further aspect, in use to facilitate formation of an arteriovenous fistula, the circumference of a proximal end of the tubular body can be less than the circumference of a distal end of the tubular body.

In general, in one embodiment, a method for inserting a device for use in creation of an arteriovenous fistula, includes the steps of identifying a candidate artery and a candidate vein, dissecting the candidate vein, inserting a device into the vein, creating a breach in the candidate artery at a desired angle and location, introducing the device and vein into the candidate artery, forming the device into a curvature angle selected to minimize turbulent blood flow in an anastomosis formed by the vein and the artery and fastening a distal portion of the device to the artery to form an anastomosis. The step of fastening the distal portion of the device to the vein to form an anastomosis can optionally include the threading distal end of the device into the vein, turning the device to engage the filament loops that comprise the tubular body into the blood vessel so that the device drives into the blood vessel and then securing the proximal end into the artery as described above.

This and other embodiments can include one or more of the following features. In one aspect, after the fastening step the anastomosis formed by the vein and the artery forms an anastomosis angle between 90 degrees and 180 degrees. In another aspect, the anastomosis angle can be between 100 degrees and 130 degrees. In yet another aspect, the fastening step can further include engaging a fastener on the distal portion of the device with a portion of the artery. In still another aspect, the fastening step can further include suturing the distal portion of the device to the artery. In another aspect, the method can further include using an angioplasty balloon to expand the vein before or after the inserting step.

In a further aspect, after the forming step or the fastening step a circumference of the proximal aperture of the device attached adjacent to the artery can be larger than a circumference of the distal aperture of the device within the distal vein. In another aspect, after the forming step or the fastening step the proximal aperture of the device attached to the artery can be configured into an imperfectly circular shape. In a further aspect, the proximal end of driven device that rests inside the dissected vein, is attached to the artery so that the tension of the vein and the support of the device maintains a natural angle for the anastomosis by means of tension: like stringing a bow.

In yet another embodiment, the device is placed into the vein by means of an introducer. The introducer or obdurator is a small cannula formed to fit the selected vein to dissect. In one embodiment, the introducer (or obdurator) is formed to receive the distal end of the filament and keep in contact when rotated in a direction to drive the device into the vein or other blood vessel. Still further, the vein can be a cephalic vein and the artery can be a radial artery. In another aspect, the forming step can further include applying heat to the device. In yet another aspect, the method can further include applying pressure to the device. In still another aspect, the forming step can be performed by inserting and inflating a balloon inserted into the device. In another aspect, the method can further include forming the desired anastomosis angle by inserting a shape tool into the device proximal aperture after insertion into the vessel.

In one embodiment there is provided a platform device for use in the creation of an arteriovenous fistula. The platform device includes a generally cylindrical device of a plurality of windings, which may be deformed to assume a desired curvature, wherein said platform is configured for attachment to an artery at its proximal aperture and for insertion into a vein at its distal aperture. In still other alternatives, the proximal aperture is connected to the desired artery at an angle selected to minimize turbulent blood flow in the arteriovenous anastomosis, the angle is between 90 and 180 degrees. In another aspect, the tube or platform device may assume a generally conical shape, where the circumference of the distal aperture is less than the circumference of the proximal aperture and, in one embodiment, the desired curvature is achieved by subjecting the coil structure to an external stimulus.

In still another aspect, there is provided a method for inserting a device for use in creation of an arteriovenous fistula. The method includes identifying a candidate artery and a candidate vein; dissecting the candidate vein; using an angioplasty balloon to expand the vein; inserting a device into the vein; creating a breach in the candidate artery at a desired angle and location; introducing the device and vein into the candidate artery; and fastening the vein to the artery. In one alternative, the device's configuration is modified by the application of an external stimulus prior to insertion into the candidate artery. These and other details of various embodiments are provided in International Patent Application No. PCT/US13/046370 which is herein incorporated by reference in its entirety.

Figure 2A:
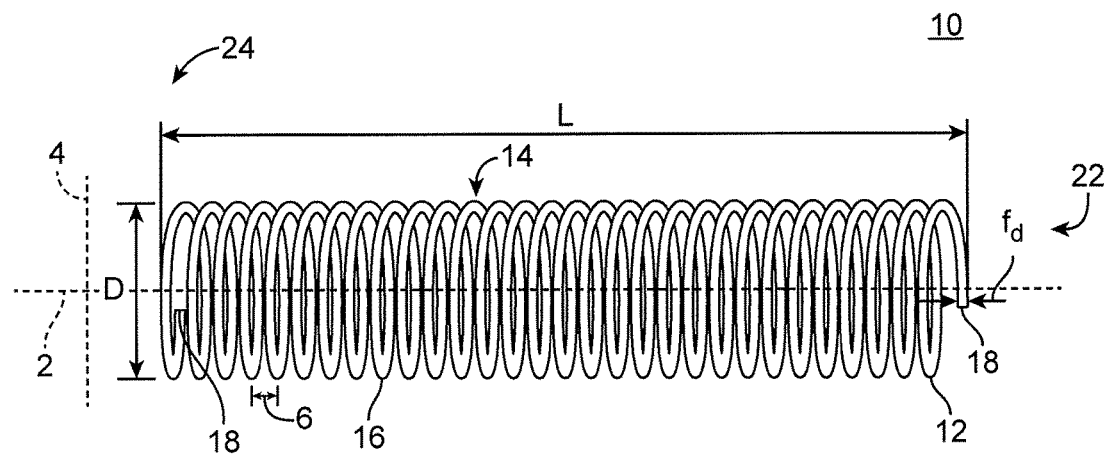
FIG. 2A is a side view of a platform device with small spacing between adjacent windings.

FIG. 2A is a side view of a platform device 10 having a plurality of windings 16 to form a coil structure 14. The platform device 10 has a proximal end 22 and a distal end 24 is formed from a filament 12. As used herein, a filament of resorbable material having overall dimensions (depending on cross section shape $f_d$) ranges from about 0.002-0.003 inches; or 0.002-0.005 inches; or from about 0.004-0.007 inches or from about 0.004-0.018 inches. In some braided filament embodiments (see FIGS. 8A and 8B below) the overall braid would have these exemplary dimensions and individual filament strands making the braid would be smaller. In general and depending upon the desired configuration, a filament 12 is cut to a desired length of from about 1 inch to about 10 inches or longer as determined by platform characteristics and anastomosis requirements. Additionally, the filament embodiments described herein may be constructed of different compositions of polylactic acid and different additives to add strength and to control the rate of resorption.

Returning to platform 10 shown in FIG. 2A, the filament 12 is formed about a major axis 2 to form the plurality of windings 16. The windings 16 are spaced apart from each adjacent winding by a spacing 6. Each winding has a width (D) that is described spanning across a minor axis 4 (i.e., across the major axis 2) of the coil structure length (L). The diameter of the windings may vary depending upon the application of the platform device. Exemplary windings may be from 2 mm to 10 mm. In some aspects, the platform device will have a winding width during use of from 2.5 mm to 4 mm, or, optionally, from 4 mm to 6 mm. The width of the windings may be increased by expanding the windings when implanted within a lumen. In the illustrated embodiment of FIG. 2A the filament 12 has a generally round cross-section and the terminal ends 18 of the filament are shown with a flat end 18. In one aspect, the illustrated embodiment of FIG. 2A shows a spacing 6 between each of the adjacent windings 16 that is small or a compact spacing. A small or compact spacing 6 between windings may be used advantageously when the platform is loaded onto a delivery device and prior to insertion into a lumen. The length of a platform device may be of any length suited to the application within the lumen. The length may also be adjusted after implantation by adjusting the spacing 6 between windings or by altering the orientation of the windings (see, for example, FIG. 2D).

Figure 2B:
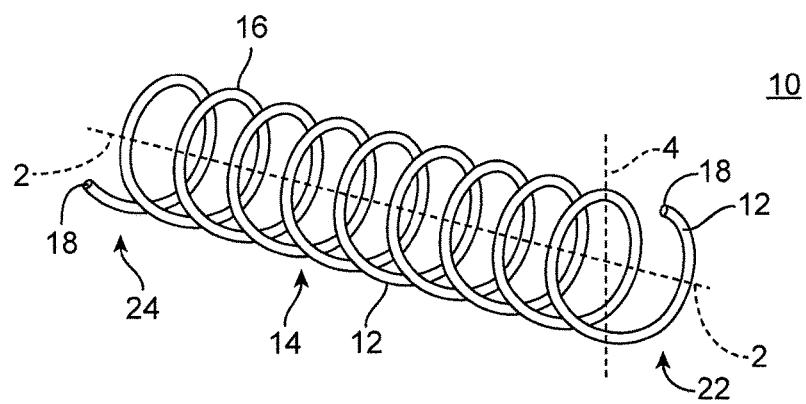
FIG. 2B is an isometric view of the platform device of FIG. 2A with increased spacing between adjacent windings.
Figure 2C:
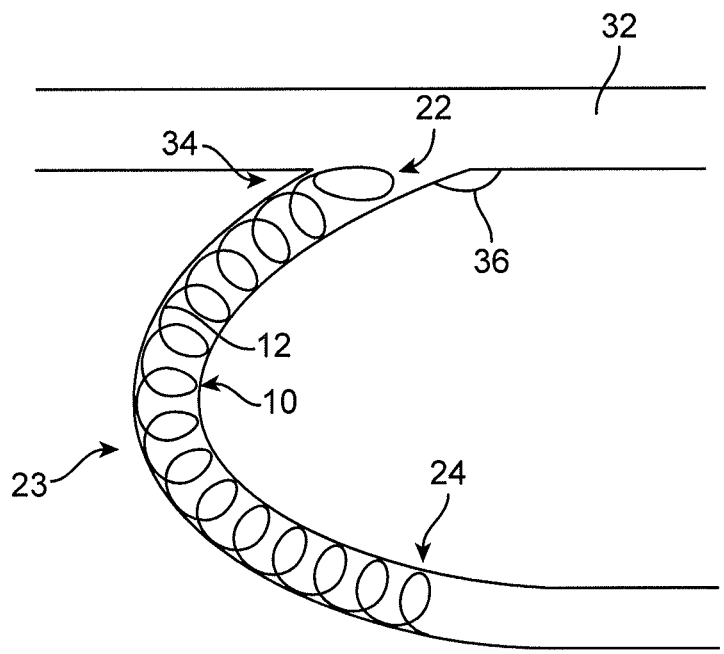
FIG. 2C is a side view of the platform of FIG. 2A, to be implanted within and shaping a vein use to form an arteriovenous fistula with and artery.

As shown in FIG. 2B, the platform 10 illustrated has increased spacing 6 between adjacent windings 16. Increased spacing 6 between adjacent windings will increase the overall length of the coil structure 14. FIG. 2C is illustrates a platform 10 (expanded as shown in FIG. 2B) in position within a vein 31 that has been attached to an artery 32. The platform proximal end 22 is used to hold open the vein 31. Adjusting the filament and/or windings also allows the shape of angle of attachment to be adapted by the surgeon. The illustrated implementation of a platform 10 within a vein 31 as shown in FIG. 2C is illustrative of the use of the platform for the formation of a hemodynamic environment conducive to AV arteriovenous fistula maturation.

Figure 2D:
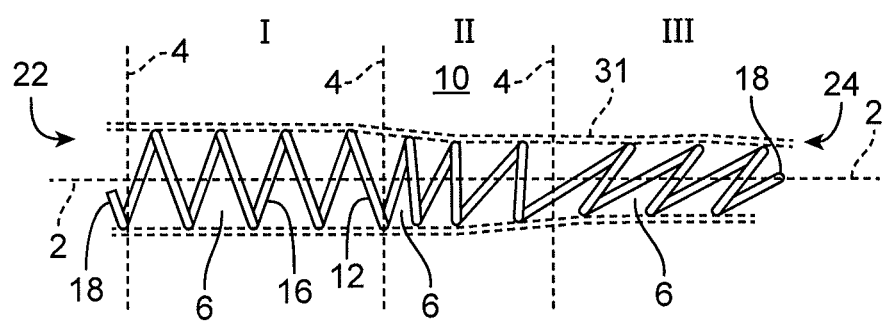
FIG. 2D is a side view of a portion of the platform illustrating how the windings and coil structure may be modified to alter the lumen.

FIG. 2D is an exemplary section view of one or more windings of the embodiment of FIG. 2C. FIG. 2D illustrates how the windings 16 within the platform may be adjusted into different spacing, overall winding shape to facilitate the formation of a desired luminal structure, orientation or shape to facilitate the desired anastomosis environment. Section I illustrates a spacing 6 that is even between adjacent windings 16. Section II illustrates a spacing 6 that varies between adjacent winding s 16. Section III illustrates how spacing 6 and the angle between adjacent windings 16 may adapt to a smaller vessel diameter.

Figure 3A:
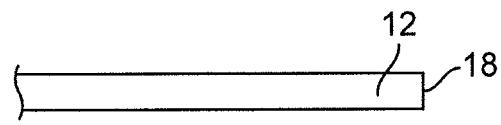
FIGS. 3A-3E are various alternative configurations of the terminal end of a filament.
Figure 3B:
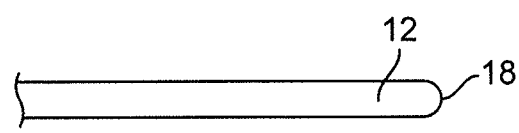
Figure 3C:
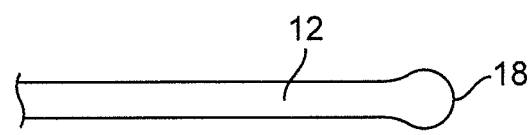
Figure 3D:
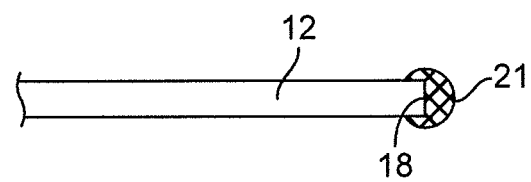
Figure 3E:
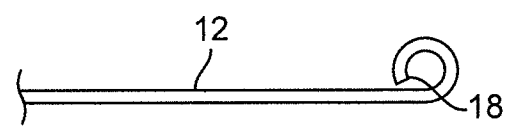

FIGS. 3A-3E illustrate a variety of different configurations of the filament 12 terminal end 18. Terminal end 18 may be shaped into a number of different configurations in order to provide an atraumatic end and reduce or minimize penetration of a lumen wall during use of the platform 10. FIG. 3A is a section view of the filament 12 having a flat terminal end 18. FIG. 3B is a section view of the filament 12 having a rounded terminal end 18 of about the same diameter as the overall filament 12 diameter. FIG. 3C is a section view of the filament 12 having an enlarged rounded or bulbous terminal end 18. The terminal end 18 of FIG. 3C is has a dimension or a diameter that is larger than overall diameter or dimension of the filament 12. FIG. 3D is a section view of a filament 12 having a flat terminal end 18 and a ball or bulb 21 mounted onto the terminal end 18. The filament 12 illustrated in FIG. 3D accomplishes an atraumatic end through the use of the rounded ball or ball 21. FIG. 3E is a section view of a filament 12 having a bent back distal portion so that the terminal end 18 is rolled back into a rounded tip.

Figure 4A:
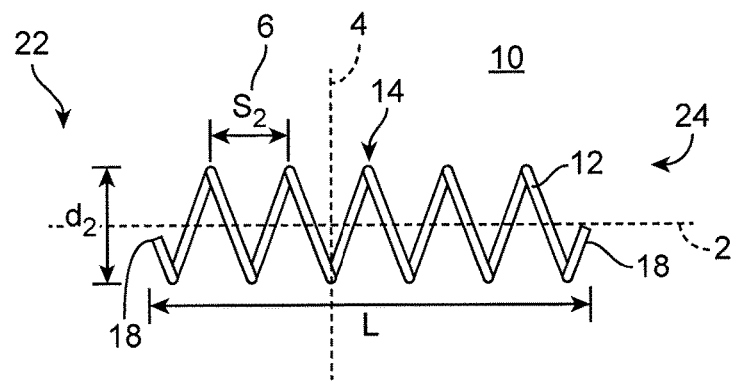
FIG. 4A is a platform embodiment having a coiled body formed of a small filament with only a few windings.
Figure 4B:
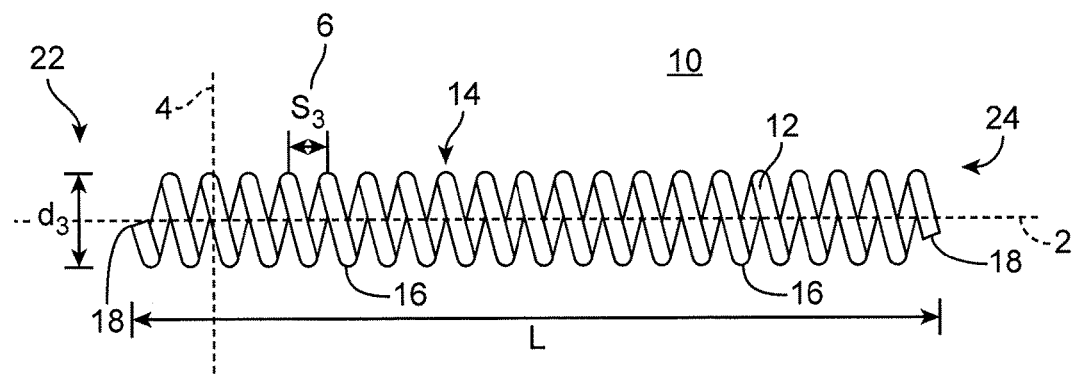
FIG. 4B is a platform embodiment having a coiled body formed by a larger filament with a large number of small windings.

FIGS. 4A and 4B illustrate various different embodiments of a platform 10. FIG. 4A illustrates a platform 10 having windings 16 with a diameter D2 and adjacent spacing 6 of S2. In contrast, FIG. 4B illustrates a platform 10 embodiment where the filament 12 has a smaller overall shape and the diameter D3 of the windings is much smaller than the diameter D2 of FIG. 4A. In addition, the adjacent windings spacing 6 ($S_3$) is much less than the adjacent windings spacing ($S_2$) shown in FIG. 4A. As will be appreciated in the description that follows, FIGS. 4A and 4B are only a few of the various different alternative embodiments of the platform 10, a filament 12, a coil structure 14 and windings 16 of the various embodiments of the present invention.

Figure 5:
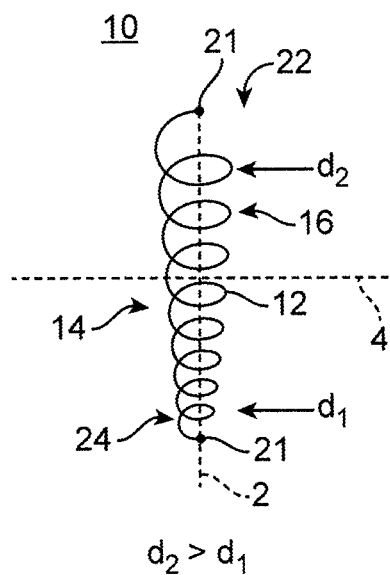
FIG. 5 is a side view of the platform device embodiment having a proximal portion with a larger diameter than a distal portion.

FIG. 5 is a perspective view of another embodiment of the platform 10. In this embodiment, the filament 12 as terminal end 18 having a rounded ends as illustrated and described with regard to FIG. 3C or 3D. In addition the windings 16 have a variable diameter from the distal end 24 to the proximal end 22. The diameter D2 at the proximal end 22 is larger than the diameter D1 at the distal end 24. In general, the platform 10 illustrated in FIG. 5 has a distal portion diameter of D1 that is smaller than a proximal portion diameter D2. Advantageously, the smaller distal portion accommodates insertion into the fixed vein while the larger proximal portion provides an adjustable opening used to attach to the artery or other lumen.

Figure 6A:
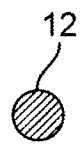
FIG. 6A is a cross-section view of the filament with a round cross-section shape.
Figure 6B:
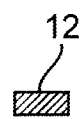
FIG. 6B is a cross-section view of the filament with a generally rectangular cross-section shape.
Figure 6C:
FIG. 6C is a cross-section view of a filament with a rounded rectangular cross section shape.
Figure 6D:
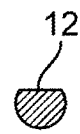
FIG. 6D is a cross-section view of the filament having a rounded shape and at least one flat side.

The filament 12 may be provided for use in the platform 10 having a variety of different sizes, shapes and overall dimensions depending upon the environment in which the platform device 10 will operate. FIGS. 6A-6D illustrate a variety of different cross-section shapes of various embodiments of the filament 12. FIG. 6A is a cross-section view of the filament 12 having a circular or round shape. FIG. 6B is a cross-section view of the filament 12 having a generally rectangular shape. FIG. 6C is a cross-section view of the filament 12 having a rounded rectangular shape. FIG. 6D is a cross-section view of the filament 12 having a cross-section shape having a rounded portion and a flat portion. A filament 12 may be extended into any of a variety of cross section shapes depending upon the design of the platform device 10 and the environment for use in an anastomosis formation.

It is to be appreciated that the orientation of the filament 12 used in a particular platform device 10 embodiment may be selected so that a desired filament orientation is obtained. In one aspect, a desired filament orientation is obtained when a particular shaped portion of a filament is positioned against a vessel wall. In another aspect, a desired filament orientation is obtained when a particular shaped portion of the filament is positioned so as to be exposed to the fluid flow within a vessel. The orientation, aspect or portion of the filament along with the shape, dimensions and properties may be adjusted as described herein to provide a favorable environment for the successful completion of an intended anastomosis. In one aspect, a filament 12 is selected so that when the associated platform device 10 is in use the filament 12 is along the lumen wall. The filament has a profile in the fluid flow that minimizes or reduces adverse impact on fluid dynamics within the lumen. In this way, the filament and platform device aid in structurally supporting the lumen post-surgery while reducing the fluid flow in the lumen that after is an important factor in the anastomosis process. The flow of blood in anastomosis of blood vessels in a particular example of this design consideration for platform device and filament 12.

Figure 7A:
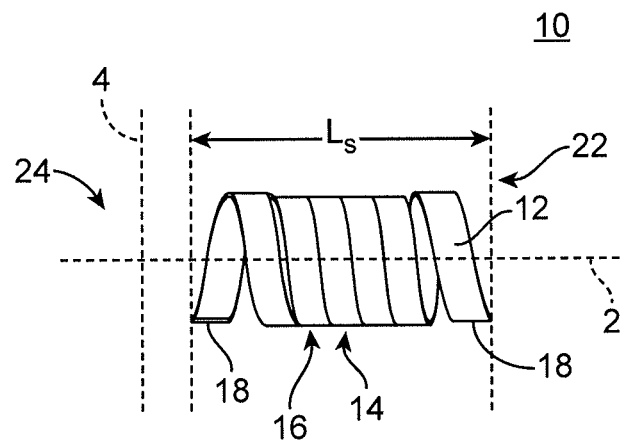
FIGS. 7A and 7B are side views of the platform device having a filament with a generally rectangular cross-section shape in a stowed or compact configuration (FIG. 7A) and a deployed or expanded configuration (FIG. 7B).
Figure 7B:
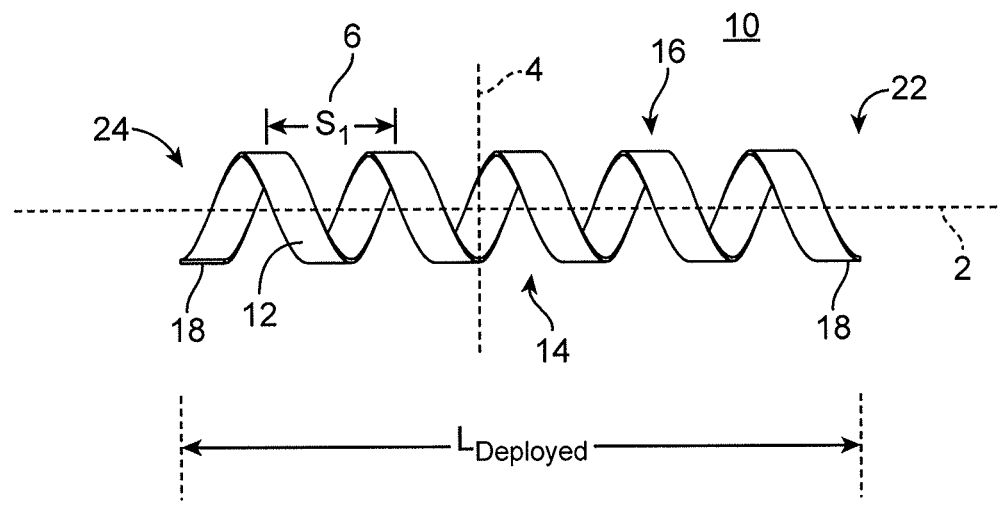

FIGS. 7A and 7B illustrate an embodiment of a platform device 10 formed from a filament 12 having a generally rectangular cross-section shape. In one aspect, the filament cross-section shape is as shown in FIG. 6B. In another aspect the filament cross-section shape is as shown in FIG. 6C. In still other aspects, the width of the filament 12 is increased and the height decreased from that illustrated in FIGS. 6B and 6C to form a filament with a form factor similar to a ribbon as illustrated in FIGS. 7A and 7B. FIG. 7A illustrates a platform 10 with a compact coil structure 14 in a stowed configuration ($L_S$). The spacing 6 between adjacent windings 16 is small, optionally, when adjacent windings 16 are in contact. FIG. 7B illustrates a platform device 10 with increased spacing 6 between adjacent windings 16 ($S_1$) as may occur in a deployed configuration. In the deployed configuration the coil structure 14 has a longer overall length ($L_{Deployed}$).

Figure 8A:
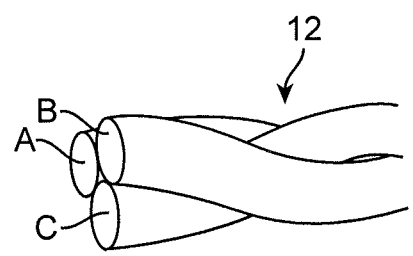
FIG. 8A is a section view of an embodiment of a three strand filament.
Figure 8B:
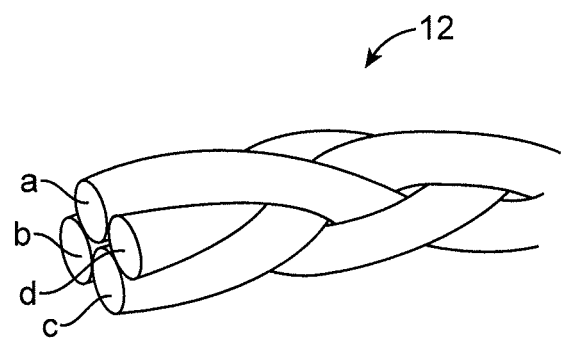
FIG. 8B is a section view of a four strand filament.

It is to be appreciated that one or more filaments 12 may be used to form an embodiment of a platform device 10 described herein. In one aspect, two or more filaments are arranged closely together as illustrated in FIGS. 8A and 8B. A multiple filament configuration is also referred to as a braided filament. Alternatively, as described elsewhere herein, two filaments may be used to form a dual coil platform structure (see platform 10 embodiments of FIGS. 10A-10C).

FIGS. 8A and 8B represent illustrative embodiments of a filament formed by 2, 3, 4 or more filament strands of biocompatible polymer. The combination of multiple smaller filaments or filament strands into a single larger filament is also referred to as a braided filament. FIG. 8A is a three filament strand braided filament for each of filament stands A, B, C has a round cross section. FIG. 8B is a four filament strand braided filament. Each of filaments a, b, c, d has a round cross section shape. The various shapes, sizes, properties and characteristics of filaments (FIGS. 6A-6D) may be applied to the filament strands in a braided filament embodiment. The size and shape of each filament strand is selected such that the overall braided filament characteristics (size, shape, biodegradability and strength profile, etc.) is provided by the aggregate properties of the individual filament strands.

FIGS. 9A-9D illustrate a partial section view of cross section filaments of three adjacent windings of the platform device. It is to be appreciated from these views how the overall filament size and shape may be used to adjust the amount of contact between the filament used in a platform and the adjacent luminal wall. While enlarged to show detail, it is to be appreciated that the overall dimension of a filament used in a platform is selected to have a size and shape so that the filament presents as low a profile as possible to the lumen interior and the intraluminal flow dynamic environment.

While each illustrative embodiment shows the filament just in opposition with the wall without luminal wall distension—other configurations are possible depending upon the clinical and the anatomical circumstances of a particular anastomosis. The characteristics of a filament and the formation of a platform device may be adjusted to provide various degrees of opposition to or forces against a lumen wall up to and including mild to moderate distention of the lumen wall by contact with the filament/platform.

Figure 9:
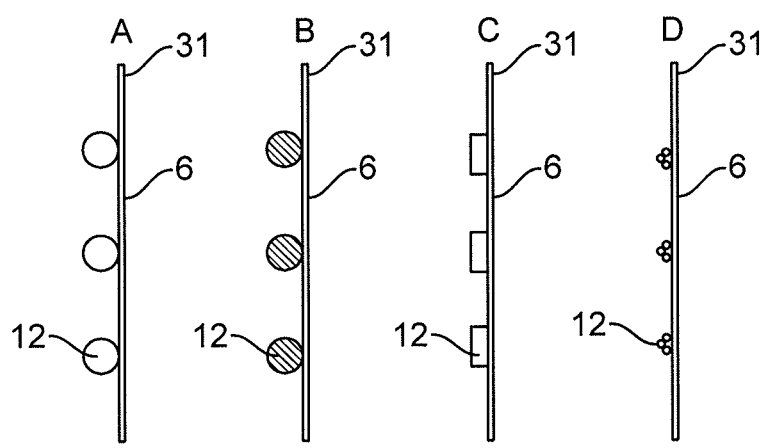

FIG. 9A illustrates the contact point of a filament 12 having a rounded cross-section shape as shown in FIG. 6A.

FIG. 9B illustrates at a section view of a multilayered biocompatible polymer formed into a rounded filament. In one aspect, properties of each filament layer may be adjusted to provide for the overall properties of the layered filament structure. For example, the layer portion adjacent to the wall may be adapted for easy absorption into the luminal wall. Similarly, one or more of the outer layers may be adjusted according to the flow properties and anatomical requirements with and the lumen or anastomosis location where the platform and filament will be used. Still further, and other alternative embodiments, the interior layers may have copolymer properties adjusted to provide for the overall strength and durability of the multilayer filament structure.

FIG. 9C illustrates a generally rectangular cross-section filament in position against the lumen wall. The rectangular cross-section shape illustrated in FIG. 9C may be, for example, as shown in FIGS. 6B, 6C or for as a filament 12 configured as shown in FIGS. 7A, 7B.

FIG. 9D illustrates a braided filament 12 in position against the luminal wall. The braided filament illustrated is similar to the configurations described above with regard to FIGS. 8A and 8B.

Figure 10A:
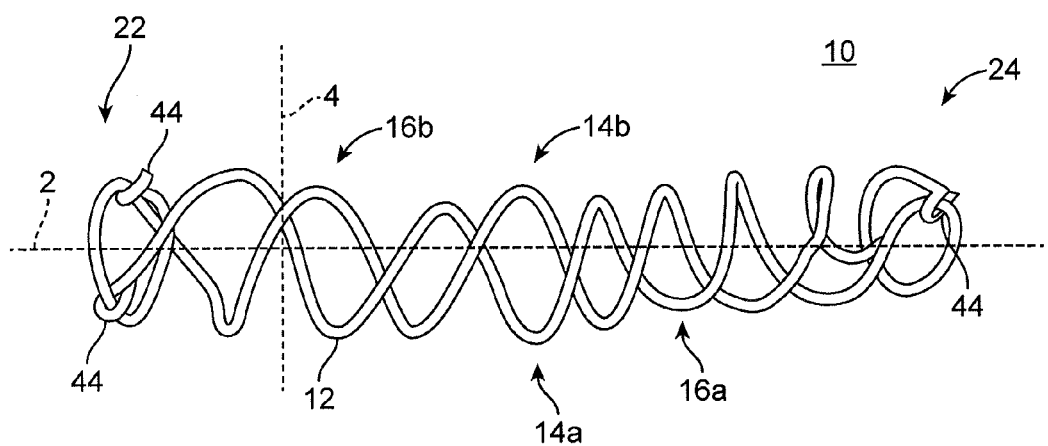
FIG. 10A is a side view of the dual filament platform device.

Similar to the braided filament structures described above, FIGS. 10A, 10B and 10C illustrate additional multi-filament platforms 10. FIG. 10A is a side view of a platform 10 formed by a single filament looped back on itself or from a pair of filaments. The illustrated platform 10 includes a pair of coiled structures 14a, 14b including a plurality of windings 16a, 16b. The terminal ends 18 are used to form knots or loops 44 to both fasten the filaments together at the proximal and distal ends as well as to provide proximal and distal openings for the platform 10. The surgeon may manipulate or adjust the filaments 12 and/or knots 44 in the double coil embodiment using standard surgical knot tying techniques to modify the platform according to the particular needs of an anastomosis site.

The dual coiled platform embodiment of FIG. 10A has a proximal end 22 and a distal end 24. In this illustrative embodiment, the proximal end 22 has two knots 44 formed in the filament. The distal end 24 has a loop and a single knot 44. One or more of the knots 44 may be a slip knot.

Optionally, the proximal and/or distal ends of the device may have filaments formed into lassos to permit easy side/shape adjustments.

In some embodiments, the filaments 12 used to form a dual filament platform 10 may be about the same shape and size or may have different shapes, sizes and properties. Moreover, the windings 16a, 16b and coil structures 14a, 14b formed by each of the filaments may be done independent of the windings and coil structure of the other filament. Still further, in various other alternative embodiments, 3, 4 or more individual filaments 12 may be used to form multiple coil embodiments of the platform 10. Additionally or alternatively, the two or more filaments 12 used in a double or multiple coil platform 10 may include single filament coils as well as braided filament coils (i.e., FIGS. 8A, 8B).

Figure 10B:
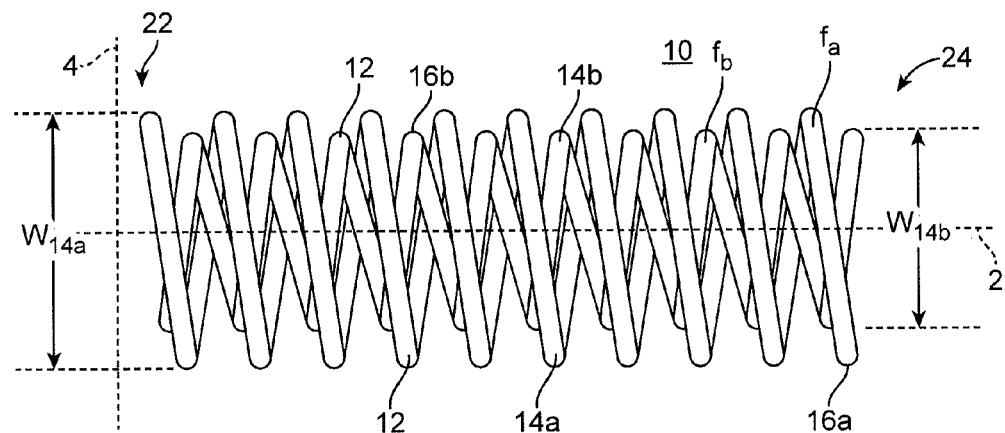
FIG. 10B is a side view of a section of a dual filament platform device.
Figure 10C:
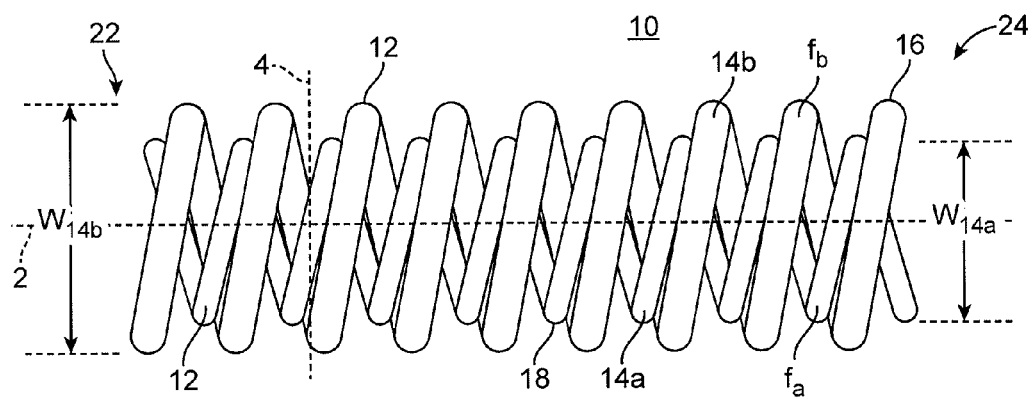
FIG. 10C is a side view of a section of a dual filament platform device.

FIGS. 10B and 10C illustrate two alternative portions of double coil platform embodiments. The proximal end distal ends and associated knots are not shown. FIG. 10 B illustrates a double coil platform embodiment where the first filament (fa) and the second filament (fb) used to make each of the coils 14a, 14b has about the same shape and size. However, the first filament (fa) forms a winding 16a with a width $W_{14a}$ that is smaller than the winding 16b formed by the second filament (fb) having a width $W_{14a}$. FIG. 10B also illustrates how the spacing 6 between adjacent windings is about the same providing coil structures 14a, 14b having approximately the same overall length.

FIG. 10C is a side view of another embodiment of a dual coil structure platform 10. In this embodiment, the overall size of each filament 12 is different (i.e., one filament is larger than the other here $f_b > f_a$). In addition, each of the coil structures 14a, 14b formed by each of the filaments $f_a$, $f_b$ has different sized windings 16a, 16b. In the illustrative embodiment, filament a is larger than filament b. In addition, the windings formed by filament a are spaced to be closer to one of the adjacent windings of filament b in contrast to the nearly even spacing of the various windings in the embodiment of FIG. 10B.

With regard to the two filament platform embodiments of FIGS. 10A, 10B and 10C, various different configurations are possible, such as, for example, forming each of the two filaments into similarly sized and shaped spiral forms. In one aspect, filaments are shaped into platforms having the form of parallel or nearly parallel spirals. As seen best in FIG. 10A (and omitted from FIGS. 10B and 10C), the distal portion of one or both filament will end with a slip knot loop that will end that portion of the platform. The other filament will be attached to that slip knot loop and will form at the opposite end of the platform an additional slip knot loop. To this slip knot loop, the other filament will be attached. The diameter of the platform can vary as the spiral forms (i.e., coil structures 14 and windings 16) of the device can be manipulated before or after implantation into a lumen or formation of an anastomosis. In addition, the length of the platform can also be adjusted by "stretching" or expanding or compressing the spiral structure (i.e., windings or coil structure) in order to have the platform cover a desired length of a lumen or anastomosis site. In still other aspects, the terminal end or a proximal or distal portion adjacent to a filament terminal end may be cut off, formed into an additional or a replacement slip knot. In still other embodiments the end of the platform or filament may be cut off and a new slip knot formed on the remaining filaments. In still further aspects, a filament may be joined to another filament by using one or more clips made of a resorbable material having properties suited to the anastomosis procedures described herein (e.g., beginning of degradation, rate of degradation and timing to complete degradation).

In one aspect, an embodiment of a platform may be placed on a delivery device to facilitate positioning of the platform within a lumen to be used in an anastomosis. Additionally, the size and cross section shape of the filament may be adjusted to provide a shape or size particular to a portion of the anastomosis site or lumen environment. For example, proximal or distal ends may be relatively larger to provide structural support. In still other embodiments, the filament may be reduced in size to permit greater flexibility such as to form a desired curvature of a lumen in an anastomosis. FIGS. 11A through 11D illustrate various different filament embodiments of an exemplary platform 10 loaded onto an illustrative obdurator 35. The obdurator 35 has a constant diameter along its length in these embodiments.

Figure 11A:
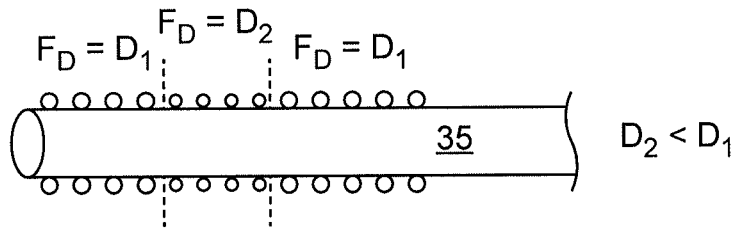
FIG. 11A is a cross-section view of an obdurator loaded with a platform device having a filament with different diameter along the length and loaded with fairly even spacing on the obdurator.

In the illustrative embodiment of a FIG. 11A, the filament 12 has a different diameter along the length of the platform. The filament 12 has a diameter D1 on the proximal and distal portions and a smaller diameter D2 positioned between them.

Figure 11B:
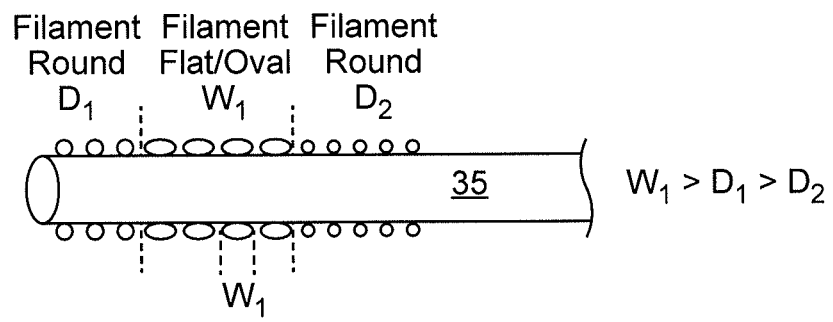
FIG. 11B is a cross-section view of an obdurator loaded with a platform device having a filament width rounded, flat and smaller rounded cross-section shapes.

In still other filament variations, the filament 12 may have a different shape in different portions of a platform 10. FIG. 11B shows a platform 10 loaded onto an obdurator 35 where the filament in the distal portion has a diameter D1 and a rounded cross-section shape and a rounded cross-section shape and smaller diameter D2 in the proximal portion. Separating the proximal and distal portions is a filament 12 having a flat or oval cross-section shape having a width W1.

Figure 11C:
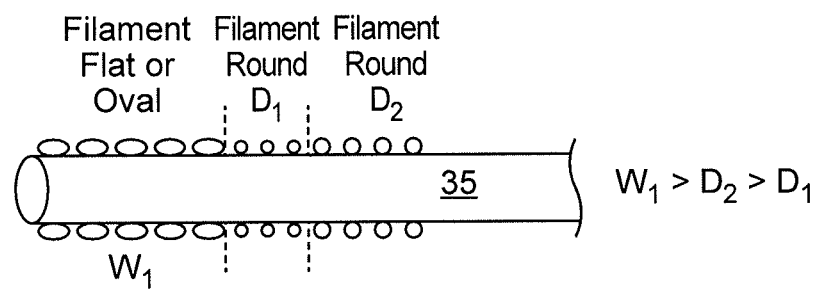
FIG. 11C is a cross-section view of an obdurator loaded with a filament having a flat, smaller rounded and larger rounded cross-section shape.

Still another filament variation is illustrated in FIG. 11C. In this illustrative embodiment of a platform 10, the filament 12 in the distal portion has a flat or oval cross-section shape and a width W1, the filament in the mid-portion has a rounded cross-section shape and a diameter of D1, and a proximal portion has a filament 12 with a round cross-section shape and a diameter D2. In one aspect, the diameter D2 is larger than the diameter D1.

Additionally or alternatively, the filament 12 may have the same, different, or a variety of different spacings between adjacent windings along the length of the coil structure 14. It is to be appreciated that reducing the spacing between windings will increase the amount of filament/length if platform thereby introducing more material/platform into the lumen. Additionally, reduced spacing upon loading and delivery provides more flexibility for a surgeon to adjust the windings/coil structure to accommodate the anatomical circumstances (i.e., see coil variations in FIG. 20).

Figure 11D:
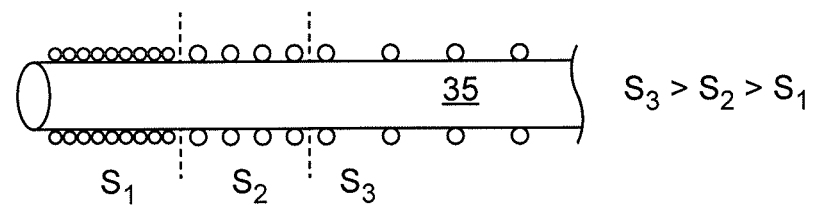
FIG. 11D is a cross-section view of an obdurator loaded with a filament having a smaller rounded and then larger rounded cross-section shapes loaded with a smaller spacing on the distal portion and increasing spacing in a proximal portion.

FIG. 11D illustrates a platform 10 on an obdurator 35 where the filament 12 is formed into windings 16 at the distal end having a spacing S1. The windings 16 and the middle portion of the platform 10 of FIG. 11D have a spacing of S2. The windings 16 in the proximal portion of the platform 10 in FIG. 11D are illustrated with a spacing S3. In this illustrative embodiment, the spacing S3 is larger than the spacing S2 which is in turn larger than the spacing S1. In this embodiment, the filament 12 used has the same size and shape but the spacing between the adjacent windings is various. For example, more coils near the distal end or a longer length of a coil structure with less material in the mid region and still less material in the proximal region may be desirous for certain anatomical locations.

Still other filament variables and embodiments are possible beyond those which are illustrated herein. Different shapes or sizes of the filament or the platform properties may be selected based on lumen properties or challenges of a particular anastomosis site. Size, shape of filament and spacing of filament windings and number of windings per unit length may be each adjusted alone or in numerous combinations to adjust the overall platform properties with respect to the lumen, anastomosis location or other factors. As a result, embodiments of the platform device may be adapted and configured whereby the length from the platform proximal portion to the distal portion is from about 2 cm, 3 cm, 4 cm, 5 cm, 6 cm, 7 cm, 8 cm, 9 cm, 10 cm, 11 cm or 12 cm before implantation into a lumen. Still further, owing to the nature of the windings and coil body adjustment and overall platform device manipulation, embodiments of the platform device may be adapted and configured whereby the length from the platform proximal portion to the distal portion is from about 2 cm, 3 cm, 4 cm, 5 cm, 6 cm, 7 cm, 8 cm, 9 cm, 10 cm, 11 cm or 12 cm after implantation into a lumen.

In still further embodiments, variations in size and shape may occur along the length of a single filament. The location of these filament characteristic variations may be specifically selected so that a particular size, shape, or orientation of shape of a filament is located in a particular portion of a lumen or anatomical site according to the specific anastomosis situation presented. Variation in filament properties permits differences in size, shape, spacing along the distal, middle or proximal portions of a platform embodiment to correspond to the various, specific anastomosis requirements depending upon the needs of a particular anatomical, clinical or physiological challenge presented for the platform use envisioned.

FIGS. 12A and 12B are top and side views respectively of an obdurator 35 having a mating feature 37 in a distal portion. The mating feature 37 is in one illustrative embodiment a cavity shaped to releasably engage the distal end of a filament and thereby secure the platform to the obdurator 35. Additionally, use of the mating feature 37 permits the obdurator to impart rotation to the platform disposed thereon to facilitate insertion into a platform lumen for use in an anastomosis (see FIG. 12D).

FIG. 12C is a side view of the abdurator of FIGS. 12A, 12B with a platform 10 loaded onto the obdurator 35. The platform distal portion 24 is loaded onto the distal portion of the abdurator. In this illustrative embodiment, the terminal end 18 of the filament 12 includes a feature 38 having a complementary and mating shape or size to facilitate coupling to mating feature 37. FIG. 12D is a side view of the embodiment of FIG. 12C inserted into a vein 31. As indicated by the arrow, the obdurator 35 is rotated so as to encourage the advancement of the obdurator and platform into the vein 31. Also visible in the view of FIG. 12D is the engagement of the complementary mating feature 38 with the feature 37.

Figure 12E:
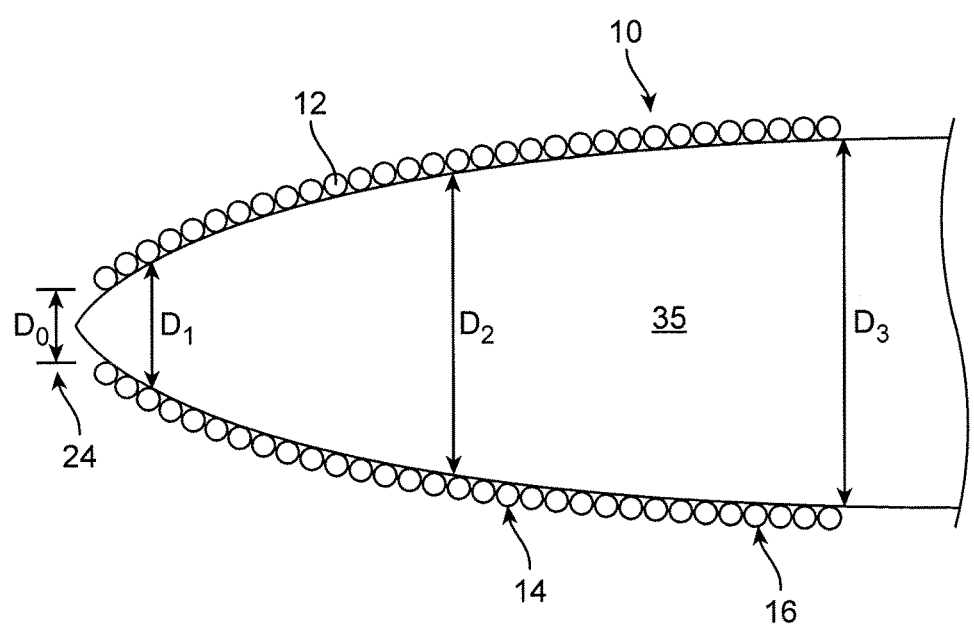
FIG. 12E is a side view of an obdurator having an increasing diameter from the proximal end to the distal end.

While the obdurator 35 may have a constant diameter along its length, other configurations are possible. Optionally, the profile of the abdurator may be selected to aid in shaping the lumen carrying the platform device 10. FIG. 12E is a cross-section view of an obdurator 35 having a generally increasing diameter from the distal end to the proximal end. In the illustrated embodiment, diameter D0 is the smallest with increasing diameter sizes from $D_1$ to an increasing D2 to the largest diameter D3. A platform 10 formed from a constant diameter filament 12 is shown in position along the distal portion of the obdurator 35 in FIG. 12E.

Figure 13:
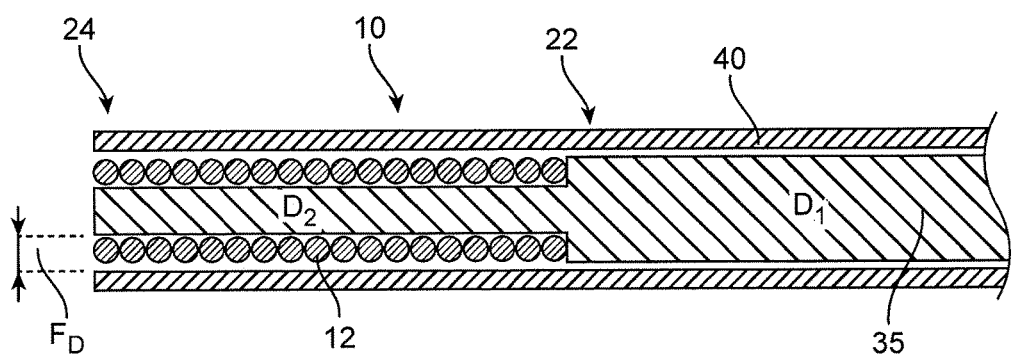
FIG. 13 is a cross-section view of the platform device loaded onto the reduced diameter distal end of an obdurator disposed within a delivery sheath.

In addition or alternatively, an obdurator 35 may have a proximal portion with the first diameter D1 that is larger than the distal portion having a second diameter D2. In the illustrated embodiment of FIG. 13 the difference in the diameter D1 and D2 is selected to accommodate the platform 10. As shown in the existing embodiment, a filament having a diameter $F_D$ is loaded onto the D2 sized portion of the obdurator 35. As a result, the overall diameter of the obdurator is nearly equal along its length as it is loaded within the sheath 40.

Figure 14:
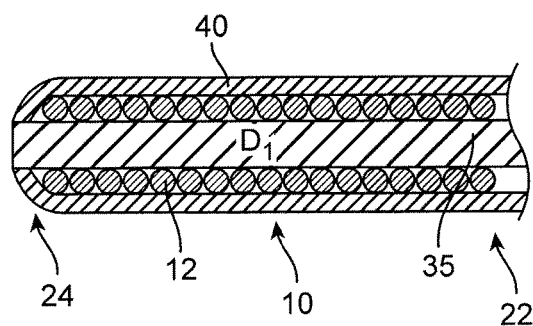
FIG. 14 is a cross-section view of the platform device loaded onto an obdurator with a delivery sheath that covers the distal portion of the platform device.

FIG. 14 is a section view of a different embodiment of a platform device loaded onto an obdurator within an introducer sheath 40. In this illustrative embodiment, the obdurator has a constant diameter. In contrast to the introducer sheath embodiment illustrated in FIG. 13, the introducer sheath 40 illustrated in FIG. 14 may extend beyond the distal most windings 16 of the distal platform device portion 24. This configuration of the introducer sheath 40 provides a tapered tip to the sheathed obdurator 35 embodiment shown in FIG. 14.

In one illustrative embodiment, the properties of the filament 12 and structure of the platform device 10 are specifically selected so as to provide a conducive environment to the formation of an anastomosis. In general, a platform 10 will provide the necessary shape, orientation, and alignment between a platform lumen and a second lumen use to form the anastomosis. In particular, the biodegradable aspects of the filament and the overall characteristics of the platform are tailored to provide initial, postsurgical structure that gives way over time in a controlled fashion as the vessels of the anastomosis heal and adapt to appropriate sizes and strength.

Figure 15A:
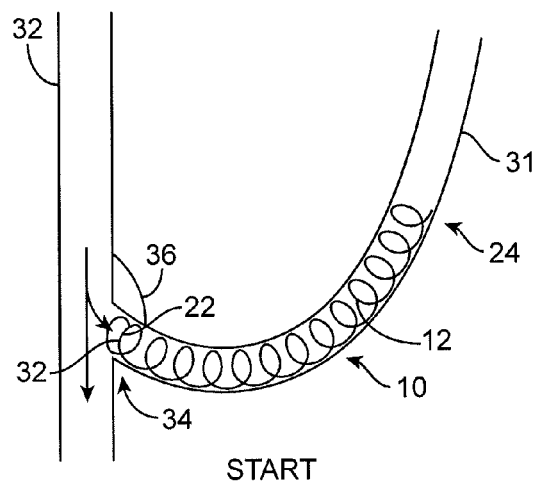
FIGS. 15A-15D illustrate, respectively, the initial (FIG. 15A) and degrading (FIG. 15B, 15C) conditions of a platform device that is finally absorbed completely (FIG. 15D).
Figure 15B:
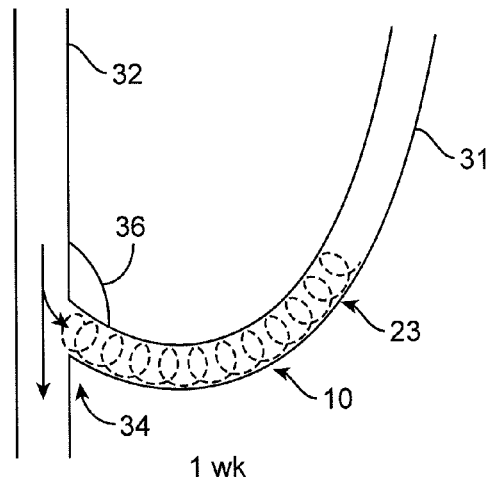
Figure 15C:
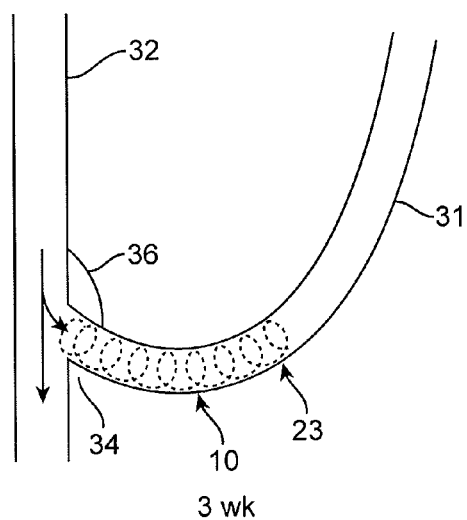
Figure 15D:
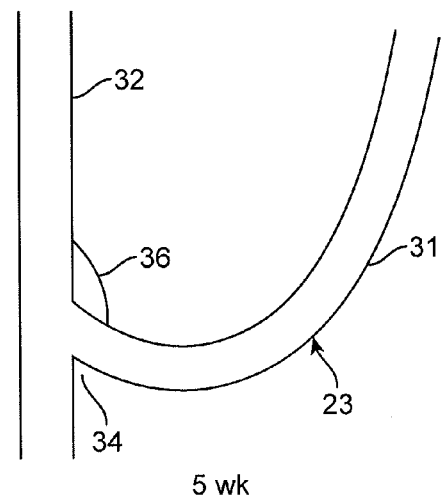

FIGS. 15A-15D illustrate, respectively, the initial platform condition (FIG. 15A) and degraded condition during absorption (FIGS. 15B, 15C) until completely absorbed (FIG. 15D). FIGS. 15A through 15D provide one exemplary platform degradation profile for an exemplary anastomosis. The platform proximal end 22 provides the shape and opening of the vein to attach to the anastomosis site.

FIG. 15A platform 10 is shown along the vein 31 adjacent to an anastomosis 34 formed with artery 32. Other profiles are possible such as total absorption of a platform after week but within 2-3 weeks or at about 3 weeks or less than 4 weeks from implantation. Initially, the platform 10 is structurally intact and is supporting the angle 36 of the vein 31 used to form the anastomosis 34. FIG. 15B illustrates the situation in the anastomosis and the platform after approximately one week. About one week after surgery, the platform 10 begins to degrade. The vein and the artery are growing as a consequence of increased blood flow provided by the additional support of the platform during the postsurgical period. The degradation and corresponding loss of strength/support of the platform to the surrounding lumen is selected to correspond to the increasing strength and potency of the lumen.

FIG. 15C is the platform supported anastomosis approximately three weeks post-surgery. The platform 10 has continued to degrade in the intervening weeks. In one illustrative embodiment, the properties of the filament 12 and the overall design of the platform device 10 would result in a platform 10 that has substantially completely dissolved by this postsurgical stage. Alternatively, in a different anastomosis situation, portions of the platform may remain and continue to provide some level of support although less than provided in prior weeks. By this stage, there is significant increase in vein and artery diameter and increasing vein wall thickness.

FIG. 15D is the platform supported anastomosis region five weeks after the surgery. In this illustrative embodiment, the platform 10 is completely removed (i.e., absorbed or biodegraded) from the surgical site. In one aspect, the illustrative anastomosis 34 is an arteriovenous fistula and it will have reached full maturation by this stage.

Figure 16A:
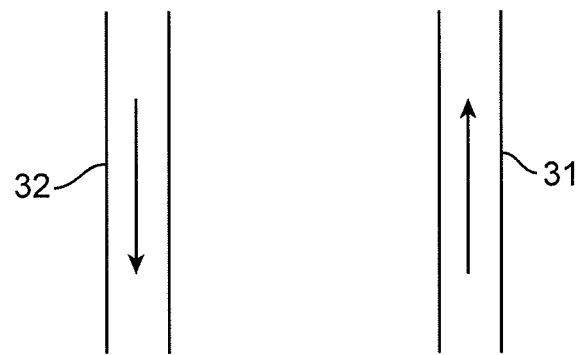
FIGS. 16A-16G illustrate a representative surgical procedure for the use of a platform device based anastomosis formation.
Figure 16B:
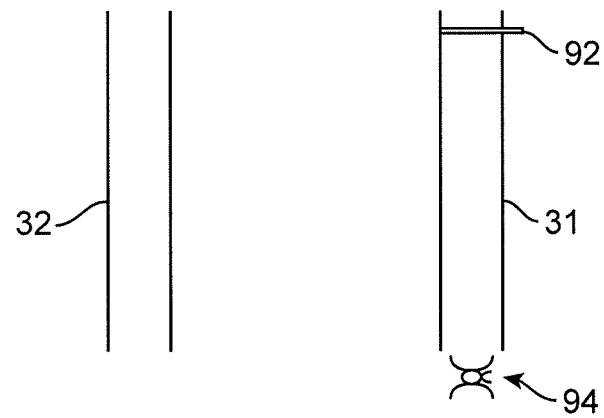
Figure 16C:
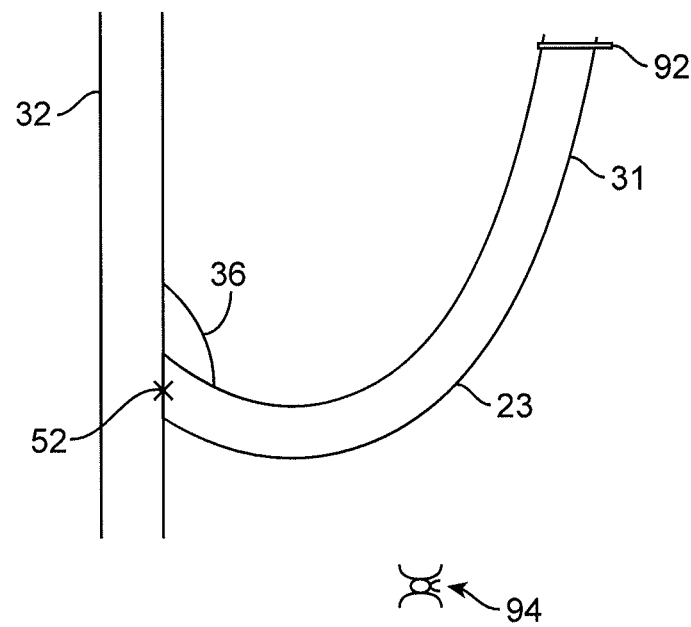
Figure 16D:
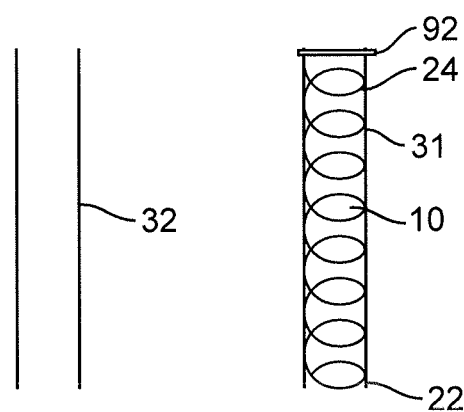
Figure 16E:
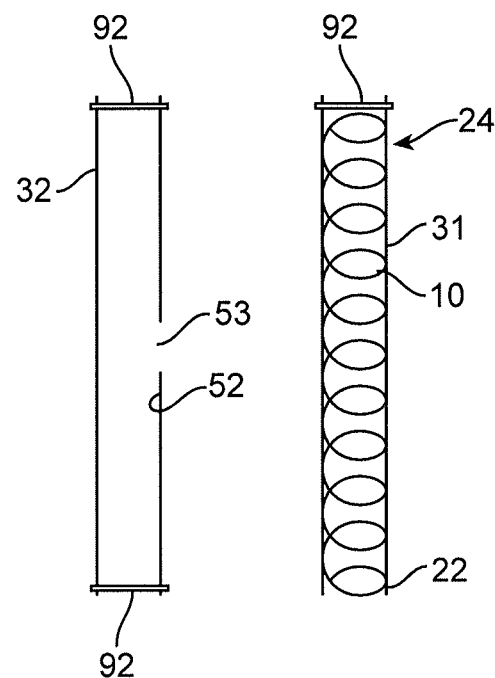
Figure 16F:
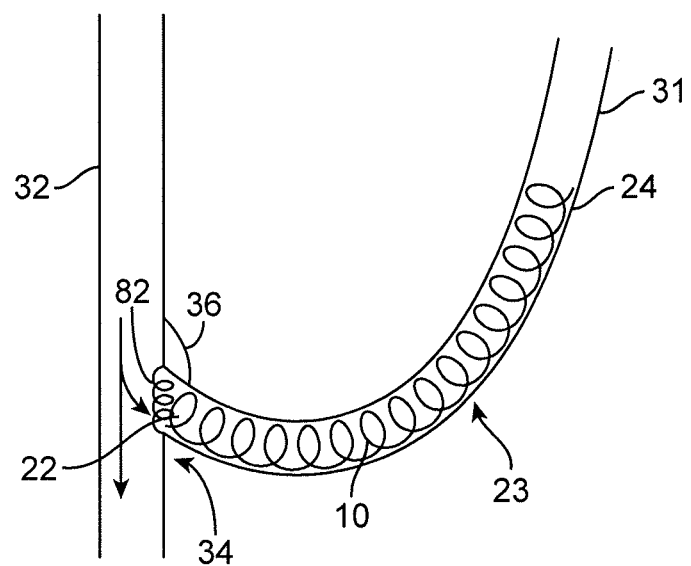

FIGS. 16A through 16G provide an illustrative surgical procedure for the use of a platform based anastomosis formation. In the exemplary procedure that follows, the anastomosis is an arteriovenous fistula and the principals and techniques may be applied to other surgical sites and conditions. First, as shown in FIG. 16A, dissect the artery 32 and vein 31 involved in the procedure. Next, as shown in FIG. 16B, ligate the distal part of the vein 94 and clamp 92 the proximal portion of vein 31 and perform a venotomy. Next, as shown in FIG. 16B bring the now mobile vein to the site 52 of the future anastomosis on the artery. Measure and evaluate the overall length of the mobile vein and the selected site on the artery for the position of the anastomosis. The desired anastomosis angle 36 is also verified in the step. Thereafter, as illustrated in FIG. 16D, load a platform 10 into the mobile vein 31m by inserting the platform into the proximal opening of the vein. Next, as in FIG. 16E, provide clamps to the artery and perform the arterial incision 53 at the site 52 of the future anastomosis. Next, as in FIG. 16F, position the proximal opening of the mobile vein or the platform lumen into contact with the arterial incision 53. The procedure concludes by suturing 82 the open proximal end of the vein to the arterial incision site 52.

The platform 10 within the vein 31 may be adjusted to provide the desired orientation, shape, or angle 36 between the vein 31 and the artery 32 at the anastomosis site 34. In this specific embodiment, the platform 10 will be adjusted so that the vein forms a desired angle and orientation to facilitate full arteriovenous fistula maturation within the desired time frame. Advantageously, the properties of the filament 12 permit the overall platform 10 to be adjusted by the surgeon during the procedure by manual manipulation of the platform. In order to provide a desired anastomosis position, the surgeon may manipulate the platform by altering the size of one or more windings or adjusting the spacing between one or more windings or altering the overall curvature of the platform within the vein. Advantageously, the number and spacing of the windings in the platform device provide a wide range of shapes and curves to accommodate a variety of different anatomical situations.

In still further aspects, a platform device 10 may be adjusted during or after the anastomosis procedure in order to provide or facilitate formation of the desired angle of the anastomosis site. FIG. 16 illustrates an embodiment of the platform illustrated in FIG. 12C in position within an anastomosis site. The surgeon may by using experience and observations or through the use of a template for measuring device, manipulate the platform 12 within the vein in order to provide the desired radius of curvature of the vein adjacent to the anastomosis site (i.e., at the junction between the vein and the artery). The overall curvature 23 of the vein may be described as having an inner radius of curvature r1 and an outer radius of curvature r2. In one aspect, the spacing between adjacent windings on the inner radius are shortened to provide adjustments to the inner radius of curvature. Optionally, spacing between windings of the platform along the outer radius of curvature may be increased to adjust the outer radius of curvature r2.

Figure 16G:
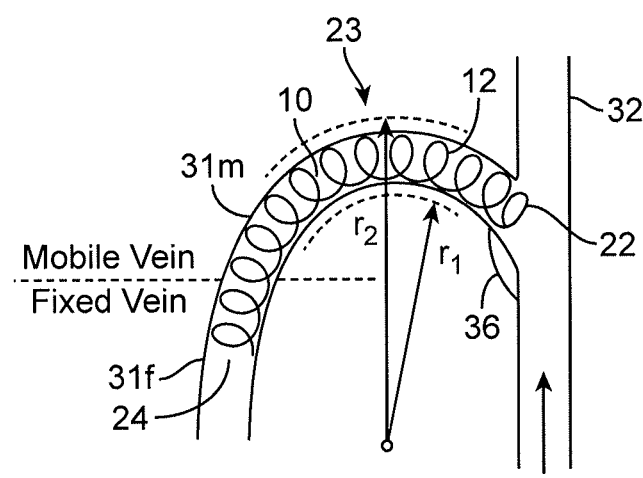

FIG. 16G also illustrates the distal platform portion 24 inserted into vein 31 into the fixes vein portion 31f (beyond the dissected or mobile vein 31m). In this way, the platform device extends between the fixed vein portion 31f at the distal end and the sutured anastomosis connection at the artery on the proximal end. In this way, the platform device is a flexible element between two fixed points that may then be used to adjust the shape of the lumen between the points.

Figure 1B:
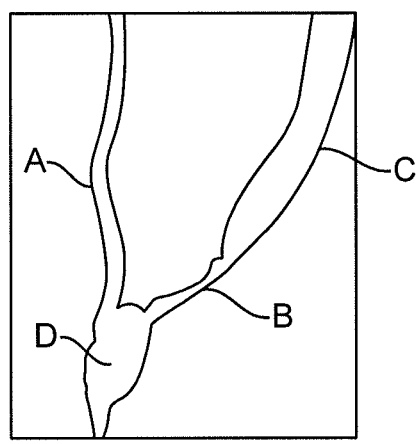
FIG. 1B is a representative view of the arteriovenous anastomosis of FIG. 1B with a non-maturation complication, a para anastomotic stenosis.
Figure 17:
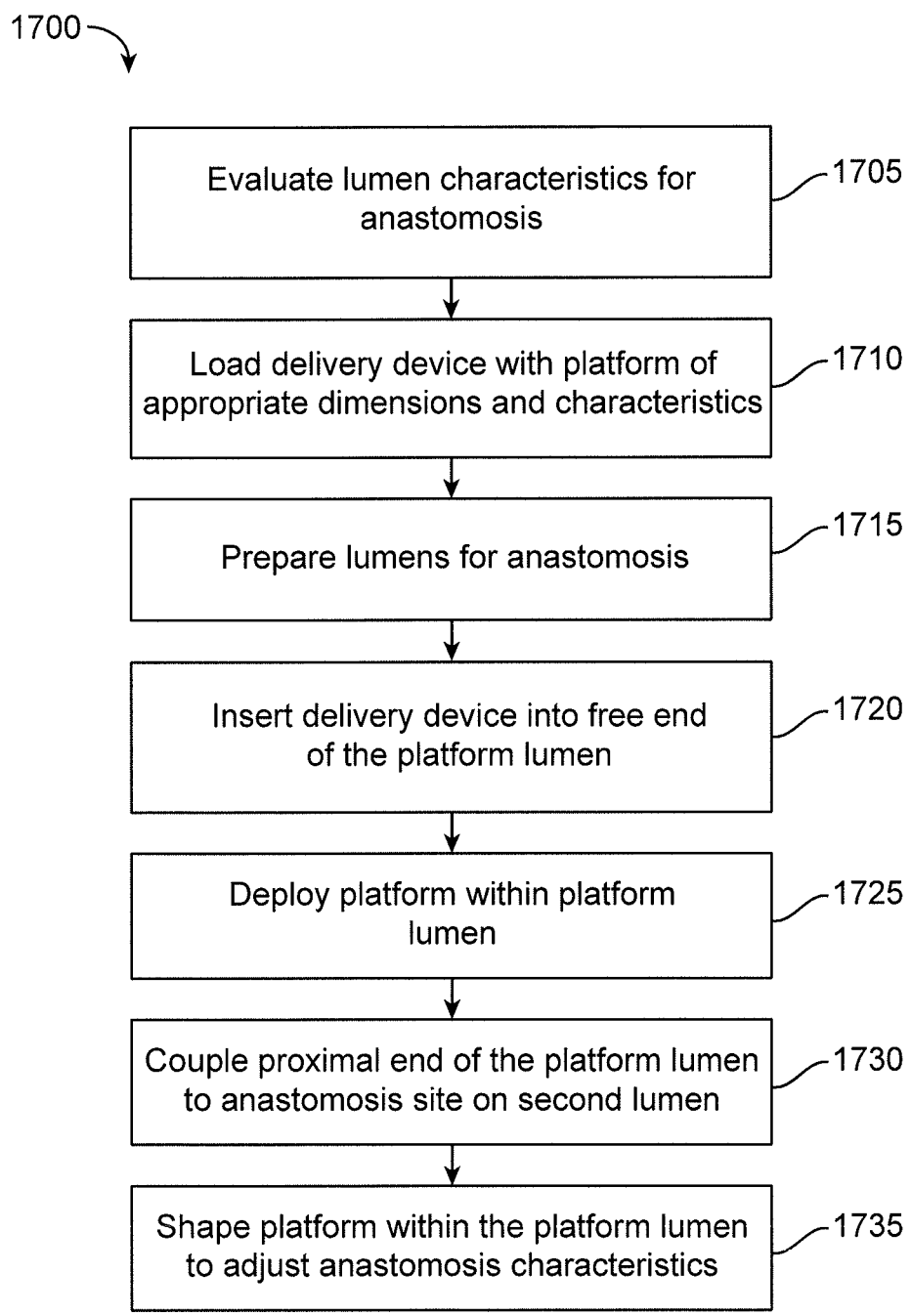
FIG. 17 is a flowchart of an exemplary platform device based method of anastomosis formation.
Figure 18B:
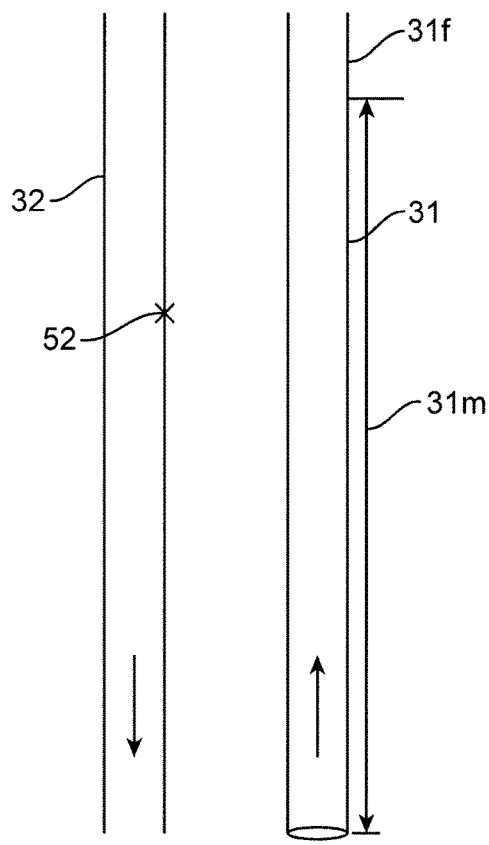
Figure 18B:
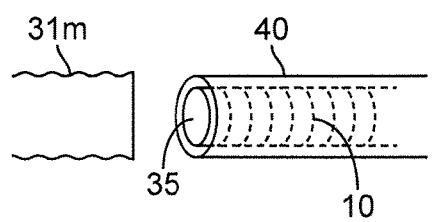
Figure 18B:
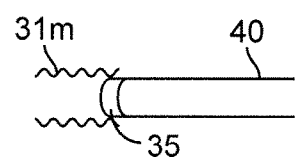

FIG. 17 is a flowchart of an exemplary platform based anastomosis formation procedure 1700. Various aspects of the illustrative surgical procedure will be described with reference to FIGS. 18A through 18G. First, at step 1705, evaluate lumen characteristics for anastomosis. As shown in FIG. 18A1 the platform lumen and the second lumen are evaluated for their relative positions as well as general size and shape along with the desired characteristics, orientation, size, shape and other factors for the anastomosis. Also shown in the view of FIG. 18A1 is the identification of the site 52 of the planned anastomosis and the second lumen 32. The platform lumen 31 is dissected along a length to provide a mobile portion 31m and a fixed portion 31f. The length of the mobile portion 31m and the relative position of the fixed portion are selected according to the desired anastomosis angle and the site of the planned anastomosis indicated in the second lumen.

Next, step 1710, load the delivery device with platform of appropriate dimensions and characteristics. FIG. 18A2 illustrates a platform 10 positioned along an obdurator 35 within an introducer sheath 40. The properties of the platform 10 including the filament characteristics, dimensions, polymer composition and other factors have been selected based upon the desired strength and degradation curves among other factors for the intended anastomosis formation. Next, step 1715, prepare the lumens for anastomosis. As shown in FIG. 18A1 and as previously described, some portion of the open procedure, ligation, or dissection of one or both of the involved lumens it may have occurred. If not by this point in the procedure, the lumens are prepared for anastomosis.

Next, at step 1720, insert the delivery device into the free end of the platform lumen. Step 1720 is illustrated in FIG. 18B. FIG. 18B illustrates the insertion of the distal portion of the introducer sheath into the open proximal end of the platform lumen. The introducer sheath is advanced distally along the platform lumen until the desired position of the distal portion of the platform is reached. In one aspect, the distal most portion of the platform will be positioned beyond the interface between the mobile platform lumen and the fixed platform lumen. In another aspect, the distal most portion of the platform will be positioned within the platform lumen at or proximal to the transition between the mobile platform lumen and the fixed platform lumen. In still another aspect, the introducer sheath is advanced into the platform lumen until a sufficient amount of the platform for the desired anastomosis characteristics is positioned within the platform lumen.

Figure 18C:
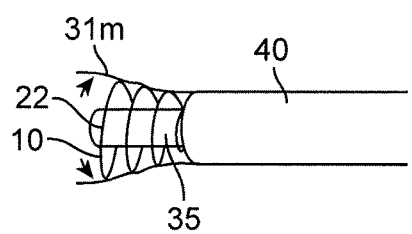

The next step of the platform based anastomosis procedure 1700 is to deploy the platform within the platform lumen. (Step 1725). This step is illustrated through the sequence of FIGS. 18C, 18D, 18E, and 18F. FIG. 18C illustrates a section view of a distal portion of the platform after the introducer sheath 40 has been withdrawn proximally to expose several of the distal most windings of the platform 10. The windings of 16 that are no longer held by the introducer sheath 40 have now expanded into a larger diameter and engaged with and opened the platform lumen. It is to be appreciated that the degree of spring back or expansion force in a platform device or filament may be adjusted depending upon the characteristics of the anastomosis is being formed.

Figure 18D:
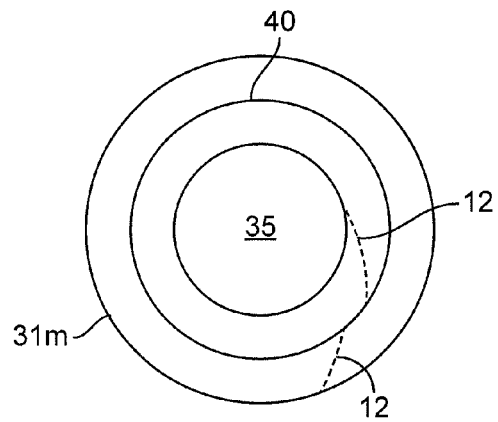
Figure 18E:
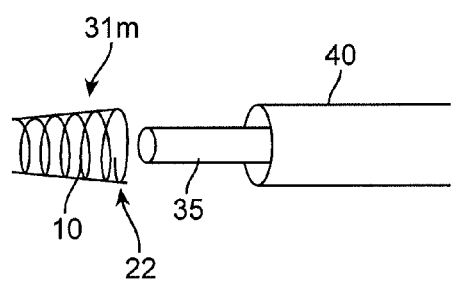
Figure 18F:
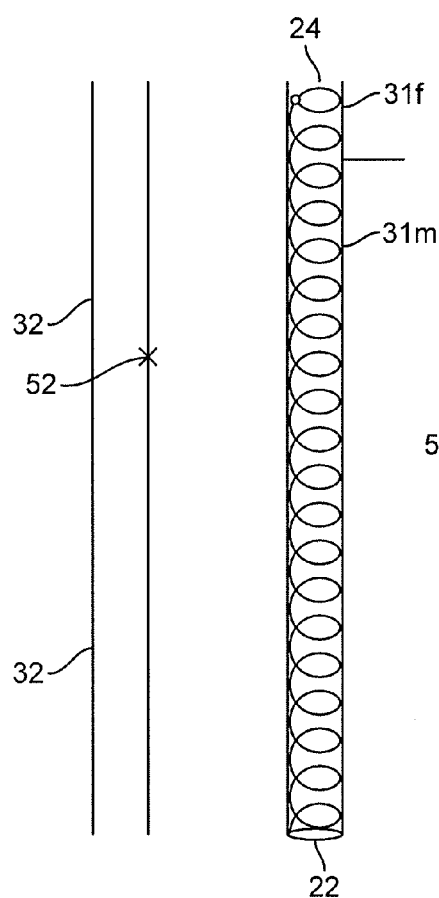

FIG. 18D is an end view of the expansion of the windings 16 illustrated in FIG. 18C. A portion of the windings 16 distal to the introducer sheath 40 is shown engaging with the interior wall of the lumen. Also shown is a more proximal portion of the platform where the windings 16 are still engaged with the introducer sheath 40. This view illustrates how the sheath is used to combine the loaded platform during insertion into the platform lumen. The platform 10 continues to be deployed in the same action by holding the obdurator 35 in position within the platform lumen while withdrawing the introducer sheath 40. Finally, as illustrated in FIG. 18D, the platform 10 is completely or substantially completely within the platform lumen, depending upon the requirements of the specified anastomosis. Additionally, the obdurator and the introducer sheath are clear of the platform lumen at the conclusion of this step. FIG. 18F illustrates a platform lumen with a platform device 10 deployed within it and prepared for attachment to the second lumen. In the illustrative embodiment of FIG. 18F, the platform 10 has been advanced within the platform lumen so that the distal most portion of the platform has a number of windings 16 within the platform lumen and beyond the demarcation point between the mobile lumen and the fixed lumen. The length of the platform 10 inserted beyond the demarcation between the mobile and fixed lumen varies depending upon the requirements of the particular anastomosis. In one embodiment, the distal most portion of the platform 10 extends on about 1 cm, 2 cm, 3 cm, or 4 cm beyond the demarcation between the mobile lumen and the fixed lumen.

Figure 18G:
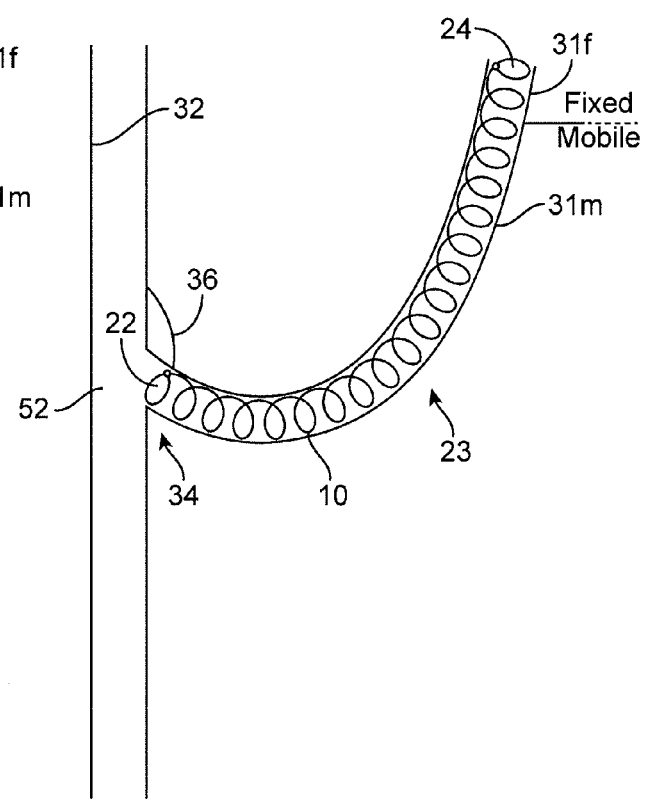

Once the platform 10 is positioned within the mobile lumen, the next step of the anastomosis procedure 1700 is to couple the proximal end of the platform lumen to an anastomosis site on the second lumen. (Step 1730). FIG. 18G illustrates one embodiment of a platform lumen attached to a second lumen. The lumen may be attached by suture, staple, or other suitable fixation device or technique suited to the anastomosis.

In this illustrative embodiment, the platform lumen is extended and supported by the platform between the two fixed points of the portion of the platform beyond the fixed mobile transition and the anastomosis site on the other lumen. In this way, the platform lumen behaves as a bow stringed between these two fixed points and may thereafter be adjusted accordingly. Additionally, positioning a platform of sufficient length so that it extends between the anastomosis point and into the fixed platform lumen portion is useful for preventing kinking of the platform lumen. Finally, at step 1735, as needed, shape the platform within the platform lumen to adjust the anastomosis as desired to achieve the desired anastomosis characteristics (i.e., see FIG. 2D). In one aspect, the platform is shaped by manual manipulation of the filament within the platform lumen to adjust the properties of the platform (spacing between windings, coil size, filament orientation, or other factors) as needed to provide the desired anastomosis environment, angle or shape of a lumen.

Figure 19:
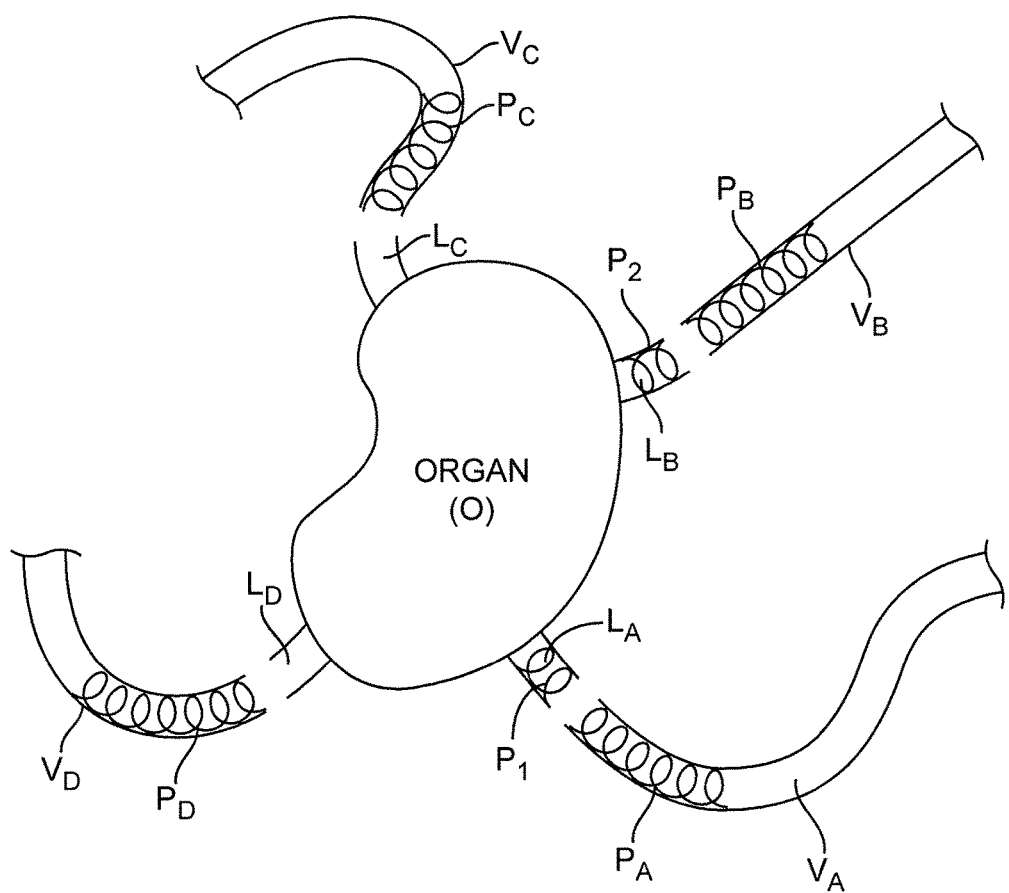
FIG. 19 is a top section view of a transplanted organ illustrating the use of various platform embodiments to enable a platform device assisted revascularization procedure where various platforms are used to open and support lumens as well as provide for shaping of vessels to be attached to the organ.

In other additional alternative embodiments, the various platform configurations described herein may be used in any of a wide range of surgical procedures where an opening in a vessel is to be maintained during the procedure or for a period thereafter. In one alternative use situation, embodiments of the platform described herein are used to facilitate the reconnection of the vasculature are to a transplant organ. FIG. 19 illustrates a top view of a transplant organ (o) having vascular lumens a-d (La-Ld). Just prior to the initiation of the revascularization during the transplant procedure, the new vasculature are provided by vessels Va-Vd have been provided with appropriately sized and configured platforms Pa-Pd. In addition, FIG. 19 also illustrates the use of appropriately sized and characterized platforms P1 and P2 for use in the organ lumens La and Lb. Platforms $P_1$ and $P_2$ may be sized and shaped to provide an appropriate mechanical assistance to ensure the opening and orientation of La and Lb is maintained. The use of platforms as described herein and as illustrated in the configuration of FIG. 19 provide for mechanical opening of the vessels involved in a transplant procedure. It is believed that the use of platforms configured as described in herein would permit the attachment of transplant vascular sure to proceed more quickly because the platforms within the vessels keep the vessel open particularly at the proximal most opening for easy attachment to the organ vasculature. Optionally or additionally, the length of the platform disposed within the vascularization lumen also provides the ability to adjust the anastomosis characteristics of each of the vessels that are attached to the transplant organ. Accordingly, FIG. 19 illustrates various different angulation (Pc, Pd and Pa) or straight (Pb) lumen positions just prior to initiation of the vascular attachment procedure.

Figure 20:
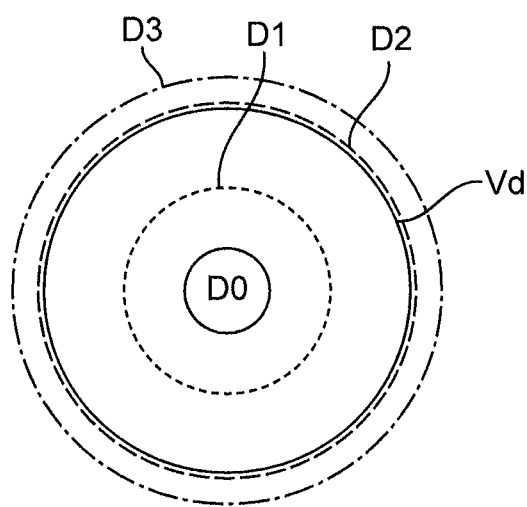
FIG. 20 is a cross-section view of an obdurator with different final platform diameters relative to an exemplary lumen diameter.

FIG. 20 illustrates an end view of a representative obdurator with various diameters of platform windings. It is to be appreciated that the various alternative embodiments, configurations, and characteristics of the filament 12 and the platform device 10 including the resulting coil structures 14 and windings 16 may be manipulated into a wide variety of structures including different response factors when deployed inside of a lumen. The resulting expansion of the windings 16 of the platform released from an introducer sheath as illustrated and described above with regard to FIGS. 18C and 18D is only one example of a property of the platform 10. By selecting the characteristics and polymer properties of the filament 12 and the associated geometry and configuration of the platform device 10 the deployment of the platform when released within a lumen may be adjusted. The variation of the platform device deployment is illustrated in the view of FIG. 20. In one embodiment the platform 10 may be configured to release from the obdurator to a representative diameter D1 that is larger than the obdurator diameter but yet smaller than the lumen diameter. In still another aspect, the platform 10 may be configured for release from the obdurator to expand to a diameter that is the same or nearly the same as the diameter of the vessel where the platform will be used. In still another aspect, the platform 10 may be configured for release from the obdurator to expand to a diameter that is larger than the diameter of the vessel where the platform will be used. In this last aspect, the platform may be oversized to the degree needed for the formation of the vessel into a desired anastomosis site. Is to be appreciated that the various different expansion properties illustrated and described with regard to FIG. 20 may be the same along the entire length of the platform. In still another alternative aspect, the expansive properties of one portion of the platform may expand more or less than an adjacent portion. In one specific aspect, a distal portion of a platform may expand to be undersized (d1) within the lumen while a more proximal portion of the same platform may be sized to deploy into the lumen into a diameter that is about the same size as the lumen (d2) or larger (d3) so as to distend the lumen.

In addition to the exemplary uses described herein, alternative embodiments and configurations of the platform device and involved filament or filaments may be selected, sized and configured for use in systems/lumens/locations/procedures within a human or animal body. Accordingly, the filament properties and platform configuration may be adapted for use in for example, in the biliary tract, within the lungs, within the guide, within the lymphatic system, within the urinary system, or within any of the lumens of the male or female reproductive system. In still other aspects, embodiments of the biocompatible filament and related platform devices may be adapted for use in blood vessels after performing an intravascular procedure. In one exemplary embodiment, the filament and platform is selected for use in a vessel after performance of an atherectomy.

In various different alternative embodiments, an anti-proliferative composition is formulated so as to be provided with the platform such as in the form of a coating on, within, along or provided by a filament, or is released by or within a portion of a multiple layer filament (see FIG. 9B) or a portion of a surface of a particular face of a filament (e.g., flat portion of filament in FIG. 6D) or provided by one or more of the filament strands of a braided filament. Exemplary anti-proliferative compositions include anti-proliferative drugs (generic name followed by trademark in parentheses):

Terazosin—(Hytrin) Antihypertensive, Benign prostatic hyperplasia therapy agent

Finasteride (Systemic)—(Propecia, Proscar) Benign prostatic hyperplasia therapy agent; hair growth stimulant, alopecia androgenetica (systemic)

Doxazosin (Systemic)—(Cardura) Antihypertensive, Benign prostatic hyperplasia therapy agent Tamsulosin (Systemic)—(Flomax) Benign prostatic hypertrophy therapy agent Prazosin (Systemic)—(Minipress) Antidote, to ergot alkaloid poisoning, Antihypertensive, Benign prostatic hyperplasia therapy agent, Vasodilator, congestive heart failure, Vasospastic therapy adjunct More examples of anti-proliferative drugs, include for example (generic name followed by trademark name in parentheses): Mitomycin for injection (Mutamycin); bleomycin sulfate for injection (Blenoxane); doxorubicin hydrochloride for injection (Adriamycin or Rubex or Doxorubicin hydrochloride); daunorubicin HCl (Cerubidine); dactinomycin for injection (Cosmegen); daunorubicin citrate (liposome) for injection (DaunoXome); doxorubicin HCl (liposome) for injection (Doxil), epirubicin hydrochloride for injection (Ellence); idarubicin hydrochloride for injection (Idamycin); plicamycin (Mithracin); pentostatin for injection (Nipent); mitoxantrone for injection (Novantrone); and valrubicin (Valstar).

In various different alternative embodiments, an anti-thrombotic composition is formulated so as to be provided with the platform such as in the form of a coating on, within, along or provided by a filament, or is released by or within a portion of a multiple layer filament (see FIG. 9B) or a portion of a surface of a particular face of a filament (e.g., flat portion of filament in FIG. 6D) or provided by one or more of the filament strands of a braided filament. Exemplary anti-thrombotic compositions include anti-thrombotic drugs (Generic Names):

Anisindione Indications: Embolism, pulmonary; Embolism, pulmonary, prophylaxis; Thrombosis; Thrombosis, prevention Antithrombin III (Human) Indications: Embolism; Thrombosis Argatroban Indications: Thrombosis; Thrombocytopenia, secondary to heparin Dicumarol Indications: Embolism, pulmonary; Embolism, pulmonary, prevention;

Fibrillation, atrial, adjunct; Occlusion, coronary, adjunct; Thrombosis; Thrombosis, prevention Heparin Sodium Indications: Coagulopathy, consumption; Dialysis, adjunct; Embolism, pulmonary; Embolism, pulmonary, prevention; Fibrillation, atrial, adjunct; Surgery, adjunct; Thrombosis; Thrombosis, prevention; Transfusion, adjunct Lepirudin (rDNA) Indications: Thrombocytopenia, secondary to heparin; Thrombosis tPA, Reteplase (generic for Retavase®), Urokinase.

In various different alternative embodiments, an anti-inflammatory composition is formulated so as to be provided with the platform such as in the form of a coating on, within, along or provided by a filament, or is released by or within a portion of a multiple layer filament (see FIG. 9B) or a portion of a surface of a particular face of a filament (e.g., flat portion of filament in FIG. 6D) or provided by one or more of the filament strands of a braided filament. Exemplary anti-inflammatory compositions include anti-inflammatory drugs:

Aspirin or Acetyl Salicylic Acid

Oral Corticosteroids (generic name followed by trademark in parentheses)—Prednisone (Deltasone), methylprenisolone (Medrol), prednisolone solution (Pediapred, Prelone)

Inhaled Corticosteroids (generic name followed by trademark in parentheses)—Flunisolide (AeroBid, AeroBid-M), triamcinolone (Azmacort), beclomethasone (Beclovent, Vanceril), budesonide (Pulmicort), fluticasone (Flovent), Nedocromil sodium (Tilade), Cromolyn sodium (Intal)

Nonsteroidal Anti-Inflamatory Agents (Generic Names):
1. Diclofenac
2. Diflunisal
3. Etodolac
4. Fenoprofen
5. Floctafenine
6. Flurbiprofen
7. Ibuprofen
8. Indomethacin
9. Ketoprofen
10. Meclofenamate
11. Mefenamic Acid
12. Meloxicam
13. Nabumetone
14. Naproxen
15. Oxaprozin
16. Phenylbutazone
17. Piroxicam
18. Rofecoxib
19. Sulindac
20. Tenoxicam
21. Tiaprofenic Acid
22. Tolmetin When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A platform device, comprising:
   a bioabsorbable filament selected to begin degrading within one week of implantation into a lumen of a human or animal body and to be substantially completely absorbed by the animal or human body after an anastomosis assistance period has elapsed;
   a coil structure having a length along a major axis and a width along a minor axis formed by a plurality of windings of the filament about the major axis wherein the filament width and the spacing between the windings relates to the coil structure length and the dimension of the windings across the minor axis relates to the coil structure width; and
   an obdurator having a distal end, a proximal end, and an overall shape adapted to receive the plurality of windings, the obdurator having a tip on the distal end and an increasing diameter of the overall shape towards the proximal end, wherein the plurality of windings are wound around the tip so that the plurality of windings have increasing winding diameters towards the proximal end.

2. The platform device of claim 1 wherein the anastomosis assistance period is less than three weeks.

3. The platform device of claim 1 wherein the anastomosis assistance period is less than five weeks.

4. The platform device of claim 1 wherein when the coil structure is in a deployed configuration the coil structure forms a selected anastomosis angle having an inner radius of curvature and an outer radius of curvature wherein the spacing between adjacent windings along the inner radius of curvature is less than the spacing between adjacent windings along the outer radius of curvature.

5. The platform device of claim 1 wherein a distal aperture of the platform device is formed into a shape selected based on a dimension or a shape of another lumen at an anastomosis site.

6. The platform device of claim 1 wherein the bioabsorbable filament is a biocompatible polymer selected from the group consisting of: a (poly)lactic acid, a poly(lactic-co-glycolic acid), a polyglycolide, a copolymer, and a cross-linked polymer.

7. The platform device of claim 1 wherein the bioabsorbable filament is a biocompatible polymer having an in vivo degradation rate corresponding to the anastomosis assistance period that corresponds to the time required for fistula formation.

8. The platform device of claim 1 wherein when the platform device is in a deployed configuration a distal aperture of the platform device has one or more windings of decreasing dimension across the minor axis.

9. The platform device of claim 8 wherein the distal aperture has a circumference and a shape selected based on an anastomosis angle of the platform device in use to form an arteriovenous fistula.

10. The platform device of claim 1, the obdurator comprising a mating feature shaped to receive a corresponding mating feature formed on a distal portion of the filament.

11. The platform device of claim 1 wherein the obdurator distal end diameter is smaller than the obdurator proximal end diameter.

12. The platform device of claim 1 further comprising an introducer sheath having a lumen dimensioned to receive the filament loaded onto the obdurator.

13. The platform device of claim 1 where the length from a platform proximal portion to a distal portion is from about 2 cm, 3 cm, 4 cm, 5 cm, 6 cm, 7 cm, 8 cm, 9 cm, 10 cm, 11 cm or 12 cm before implantation into a lumen.

14. A method for inserting a platform device for use in creation of an arteriovenous fistula, comprising the steps of:
providing a bioabsorbable filament selected to begin degrading within one week of implantation into a lumen of a human or animal body and to be substantially completely absorbed by the animal or human body after an anastomosis assistance period has elapsed;
forming a coil structure having a length along a major axis and a width along a minor axis formed by a plurality of windings of the filament about the major axis wherein the filament width and the spacing between the windings relates to the coil structure length and the dimension of the windings across the minor axis relates to the coil structure width;
loading the coil structure onto an obdurator to form the platform device, the obdurator having a distal end, a proximal end, and an overall shape adapted to receive the plurality of windings, the obdurator having a tip on the distal end and an increasing diameter of the overall shape towards the proximal end, wherein the plurality of windings are wound around the tip so that the plurality of windings have increasing winding diameters towards the proximal end;
identifying a candidate artery and a candidate vein;
dissecting the candidate vein;
inserting the platform device into the candidate vein;
creating a breach in the candidate artery at a desired angle and location;
forming an anastomosis by attaching the candidate vein to the candidate artery; and
manipulating the platform device into a shape selected to minimize turbulent blood flow in the anastomosis.

* * * * *